United States Patent [19]
Pandey et al.

[11] Patent Number: 5,807,888
[45] Date of Patent: Sep. 15, 1998

[54] PREPARATION OF BROMINATED PACLITAXEL ANALOGUES AND THEIR USE AS EFFECTIVE ANTITUMOR AGENTS

[75] Inventors: Ramesh C. Pandey, Highland Park; Luben K. Yankov, Edison; Raghu Nair, Bridgewater; Alex Pouley, Highland Park, all of N.J.

[73] Assignee: Xechem International, Inc., New Brunswick, N.J.

[21] Appl. No.: 654,424

[22] Filed: May 29, 1996

Related U.S. Application Data

[63] Continuation-in-part of Ser. No. 571,427, Dec. 13, 1995, abandoned.

[51] Int. Cl.⁶ .................... A61K 31/335; C07D 305/14
[52] U.S. Cl. ................... 514/449; 549/510; 549/511
[58] Field of Search .................. 549/510, 511; 514/449

[56] References Cited

U.S. PATENT DOCUMENTS

| | | | |
|---|---|---|---|
| 4,814,470 | 3/1989 | Colin et al. | 514/449 |
| 4,924,011 | 5/1990 | Denis et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,019,504 | 5/1991 | Christen et al. | 435/123 |
| 5,059,699 | 10/1991 | Kingston et al. | 549/511 |
| 5,136,060 | 8/1992 | Holton | 549/510 |
| 5,157,049 | 10/1992 | Haugwitz et al. | 514/449 |
| 5,175,315 | 12/1992 | Holton | 549/510 |
| 5,194,635 | 3/1993 | Kingston et al. | 549/430 |
| 5,200,534 | 4/1993 | Rao | 549/510 |
| 5,202,448 | 4/1993 | Carver et al. | 549/510 |
| 5,227,400 | 7/1993 | Holton et al. | 514/444 |
| 5,229,526 | 7/1993 | Holton | 549/213 |
| 5,243,045 | 9/1993 | Holton et al. | 544/60 |
| 5,248,796 | 9/1993 | Chen et al. | 549/510 |
| 5,250,683 | 10/1993 | Holton et al. | 544/60 |
| 5,250,722 | 10/1993 | Bombardelli et al. | 560/104 |
| 5,254,580 | 10/1993 | Chen et al. | 514/449 |
| 5,254,703 | 10/1993 | Holton | 549/510 |
| 5,272,171 | 12/1993 | Ueda et al. | 514/449 |
| 5,274,124 | 12/1993 | Holton | 549/214 |
| 5,278,324 | 1/1994 | Kingston et al. | 549/510 |
| 5,279,949 | 1/1994 | Nair | 435/123 |
| 5,283,253 | 2/1994 | Holton et al. | 514/444 |
| 5,284,864 | 2/1994 | Holton et al. | 514/449 |
| 5,284,865 | 2/1994 | Holton et al. | 514/449 |
| 5,294,637 | 3/1994 | Chen et al. | 514/449 |
| 5,296,506 | 3/1994 | Kingston et al. | 514/449 |
| 5,300,638 | 4/1994 | Farina et al. | 540/357 |
| 5,310,672 | 5/1994 | Wann et al. | 435/240 |
| 5,319,112 | 6/1994 | Kingston et al. | 549/510 |
| 5,334,732 | 8/1994 | Murray et al. | 549/510 |
| 5,336,684 | 8/1994 | Murray et al. | 514/449 |
| 5,336,785 | 8/1994 | Holton | 549/214 |
| 5,338,872 | 8/1994 | Holton et al. | 549/510 |
| 5,412,092 | 5/1995 | Rey et al. | 540/200 |
| 5,470,866 | 11/1995 | Kingston et al. | 514/376 |
| 5,473,055 | 12/1995 | Mongelli et al. | 530/329 |
| 5,475,011 | 12/1995 | Ojima et al. | 514/320 |
| 5,475,120 | 12/1995 | Rao | 549/510 |

OTHER PUBLICATIONS

Rimoldi et al., J. Nat. Pro.,1996, 59(2), pp. 167–168.

*Primary Examiner*—Ba K. Trinh
*Attorney, Agent, or Firm*—Duane, Morris & Heckscher LLP

[57] ABSTRACT

Provided are novel paclitaxel analogues, namely selectively brominated stereospecific derivatives of cephalomannine and 7-epi-cephalomannine having in vivo and in vitro paclitaxel-like antitumor efficacy, methods of preparation therefor and methods for treating tumors with these compounds.

14 Claims, 29 Drawing Sheets

FIG. 12A

| FIG. 12 | |
|---|---|
| FIG.12A | FIG.12B |
| FIG.12C | FIG.12D |
| FIG.12E | FIG.12F |

"ANOLOG"
DATA SHEET

| | Time | | Mean Optical Densities | | | | |
|---|---|---|---|---|---|---|---|
| | | | | Log10 Concentration | | | |
| Panel/Cell Line | Zero | Ctrl | -8.0 | -7.0 | -6.0 | -5.0 | -4.0 |
| Leukemia | | | | | | | |
| CCRF-CFM | 0.260 | 0.852 | 0.359 | 0.345 | 0.347 | 0.294 | 0.375 |
| HL-60(TB) | 0.433 | 1.471 | 0.361 | 0.314 | 0.333 | 0.269 | 0.283 |
| MOLT-4 | 0.343 | 1.327 | 0.678 | 0.584 | 0.501 | 0.417 | 0.283 |
| RPMI-8226 | 0.786 | 1.748 | 0.924 | .911 | 0.881 | 0.798 | 0.764 |
| SR | 0.331 | 1.056 | 0.354 | 0.325 | 0.310 | 0.270 | 0.348 |
| Non-Small Cell Lung Cancer | | | | | | | |
| A549/ATCC | 0.343 | 1.981 | 1.058 | 0.799 | 0.738 | 0.754 | 0.199 |
| EKVX | 0.398 | 1.133 | 0.977 | 0.897 | 0.771 | 0.706 | 0.252 |
| HOP-62 | 0.611 | 1.628 | 1.222 | 0.765 | 0.723 | 0.706 | |
| HOP-92 | 0.747 | 1.111 | 0.950 | 0.912 | 0.925 | 0.819 | 0.025 |
| NCI-H226 | 0.543 | 1.155 | 0.795 | 0.685 | 0.637 | 0.657 | 0.071 |
| NCI-H23 | 0.389 | 1.456 | 0.528 | 0.374 | 0.388 | 0.481 | 0.009 |
| NCI-H322M | 0.592 | 1.583 | 1.060 | 0.826 | 0.818 | 0.819 | 0.083 |
| NCI-H460 | 0.159 | 1.646 | 0.385 | 0.227 | 0.214 | 0.207 | 0.016 |
| NCI-H522 | 0.462 | 0.939 | 0.396 | 0.238 | 0.155 | 0.191 | 0.024 |
| Colon Cancer | | | | | | | |
| COLO 205 | 0.222 | 1.278 | 0.149 | 0.104 | 0.097 | 0.125 | -0.007 |
| HCC-2998 | 0.372 | 1.602 | 0.799 | 0.550 | 0.477 | 0.483 | 0.111 |
| HCT-166 | 0.141 | 1.730 | 0.343 | 0.305 | 0.282 | 0.335 | 0.003 |
| HT29 | 0.090 | 0.926 | 0.109 | 0.096 | 0.054 | 0.062 | 0.001 |
| KM12 | 0.230 | 1.298 | 0.371 | 0.317 | 0.310 | 0.314 | 0.051 |
| SW-620 | 0.139 | 1.259 | 0.456 | 0.475 | 0.445 | 0.436 | 0.003 |

FIG. 12B

"ANOLOG"

Log10 Concentration

| Percent Growth | | | | | | DATA SHEET | | |
|---|---|---|---|---|---|---|---|---|
| -8.0 | -7.0 | -6.0 | -5.0 | -4.0 | | GI50 | TGI | LC50 |
| 17 | 14 | 15 | 6 | 19 | | <1.00E-08 | >1.00E-04 | >1.00E-04 |
| -17 | -28 | -23 | -36 | -35 | | <1.00E-08 | <1.00E-08 | >1.00E-04 |
| 34 | 24 | 16 | 8 | -17 | | <1.00E-08 | 2.00E-05 | >1.00E-04 |
| 14 | 13 | 10 | 1 | -3 | | <1.00E-08 | 1.97E-05 | >1.00E-04 |
| 3 | -2 | -6 | -18 | 2 | | <1.00E-08 | . | >1.00E-04 |
| | | | | | | | | |
| 44 | 28 | 24 | 25 | -42 | | <1.00E-08 | 2.37E-05 | >1.00E-04 |
| 79 | 68 | 51 | 42 | -37 | | 1.18E-06 | 3.41E-05 | >1.00E-04 |
| 60 | 15 | 11 | 9 | -100 | | 1.67E-08 | 1.22E-05 | 3.49E-05 |
| 56 | 45 | 49 | 20 | -97 | | 3.60E-08 | 1.48E-05 | 3.97E-05 |
| 41 | 23 | 15 | 19 | -87 | | <1.00E-08 | 1.50E-05 | 4.47E-05 |
| 13 | -4 | 0 | 9 | -98 | | <1.00E-08 | . | 3.57E-05 |
| 47 | 24 | 23 | 23 | -86 | | <1.00E-08 | 1.62E-05 | 4.68E-05 |
| 15 | 5 | 4 | 3 | -90 | | <1.00E-08 | 1.08E-05 | 3.71E-05 |
| -14 | -48 | -66 | -59 | -95 | | <1.00E-08 | <1.00E-08 | 1.21E-07 |
| | | | | | | | | |
| -33 | -53 | -56 | -44 | -100 | | <1.00E-08 | <1.00E-08 | 5.55E-05 |
| 35 | 14 | 8 | 9 | -70 | | <1.00E-08 | 1.30E-05 | 3.67E-05 |
| 13 | 10 | 9 | 12 | -98 | | <1.00E-08 | 1.29E-05 | 1.90E-05 |
| 2 | 1 | -40 | -31 | -99 | | <1.00E-08 | 1.04E-07 | . |
| 13 | 8 | 7 | 8 | -76 | | <1.00E-08 | 1.23E-05 | 4.73E-05 |
| 28 | 30 | 27 | 27 | -98 | | <1.00E-08 | 1.64E-05 | 4.13E-05 |

"ANOLOG" DATA SHEET

| | | | | | | | |
|---|---|---|---|---|---|---|---|
| 45 | 32 | 24 | 12 | -83 | <1.00E-08 | 1.35E-05 | 4.52E-05 |
| 66 | 32 | 10 | 10 | -91 | 2.94E-08 | 1.25E-05 | 3.92E-05 |
| 13 | -12 | -36 | -11 | -83 | <1.00E-08 | 3.34E-08 | 3.46E-05 |
| 62 | 40 | 29 | 33 | -33 | 3.49E-08 | 3.18E-05 | >1.00E-04 |
| 36 | -15 | -34 | 0 | -49 | <1.00E-08 | 5.04E-08 | >1.00E-04 |
| 25 | 18 | 14 | 14 | -95 | <1.00E-08 | 1.34E-05 | 3.86E-05 |
| 42 | 30 | 26 | -20 | -95 | <1.00E-08 | 3.86E-06 | 2.53E-05 |
| 46 | 38 | 17 | 36 | -100 | <1.00E-08 | 1.85E-05 | 4.30E-05 |
| 49 | 11 | -47 | 1 | -90 | <1.00E-08 | | 3.64E-05 |
| 17 | -11 | -14 | 16 | -94 | <1.00E-08 | | 3.98E-05 |
| 46 | 42 | 48 | 45 | -92 | <1.00E-08 | 2.13E-05 | 4.96E-05 |
| 23 | 15 | 15 | 22 | -79 | <1.00E-08 | 1.64E-05 | 5.15E-05 |
| 42 | 35 | 36 | 41 | -97 | <1.00E-08 | 1.99E-05 | 4.58E-05 |
| 38 | 24 | 15 | 22 | -97 | <1.00E-08 | 1.52E-05 | 4.00E-05 |
| 38 | 30 | 25 | 24 | -80 | <1.00E-08 | 1.70E-05 | 5.16E-05 |
| 4 | -9 | -23 | -9 | -99 | <1.00E-08 | 1.99E-08 | 2.83E-05 |
| 61 | 57 | 52 | 35 | -96 | 1.36E-06 | 1.86E-05 | 4.48E-05 |
| 21 | 15 | 8 | 11 | -93 | <1.00E-08 | 1.28E-05 | 3.86E-05 |
| 28 | 15 | 10 | 11 | -44 | <1.00E-08 | 1.59E-05 | >1.00E-04 |
| 35 | 17 | 5 | 6 | -65 | <1.00E-08 | 1.20E-05 | 6.13E-05 |

FIG. 12D

"ANOLOG"
DATA SHEET

| | | | | | | | |
|---|---|---|---|---|---|---|---|
| Renal Cancer | | | | | | | |
| 786-0 | 0.171 | 0.668 | 0.492 | 0.359 | 0.242 | 0.242 | 0.019 |
| A498 | 0.775 | 1.523 | 1.295 | 1.105 | 0.982 | 1.147 | 0.183 |
| ACHN | 0.444 | 1.624 | 1.442 | 1.170 | 0.921 | 0.905 | 0.010 |
| CAKI-1 | 0.379 | 1.003 | 0.969 | 0.823 | 0.605 | 0.385 | 0.007 |
| RXF-393 | 0.462 | 1.023 | 0.656 | 0.499 | 0.359 | 0.428 | 0.038 |
| SN12C | 0.374 | 1.666 | 0.781 | 0.676 | 0.645 | 0.612 | 0.006 |
| TK-10 | 0.667 | 1.278 | 1.243 | 1.071 | 0.902 | 0.837 | 0.366 |
| UO-31 | 0.414 | 1.102 | 1.104 | 1.014 | 0.708 | 0.601 | 0.002 |
| Prostate Cancer | | | | | | | |
| PC-3 | 0.440 | 1.737 | 0.824 | 0.644 | 0.584 | 0.606 | 0.056 |
| DU-145 | 0.312 | 1.646 | 0.606 | 0.424 | 0.295 | 0.350 | 0.079 |
| Breast Cancer | | | | | | | |
| MCF7 | 0.186 | 0.544 | 0.133 | 0.155 | 0.141 | 0.158 | 0.003 |
| MCF7/ADR-RES | 0.455 | 1.201 | 1.275 | 1.171 | 1.067 | 0.643 | 0.107 |
| MDA-MB-231/ATCC | 0.265 | 0.614 | 0.421 | 0.292 | 0.255 | 0.244 | 0.007 |
| HS 578T | 0.636 | 1.176 | 0.678 | 0.559 | 0.500 | 0.512 | 0.450 |
| MDA-MB-435 | 0.165 | 1.185 | 0.078 | 0.053 | 0.079 | 0.143 | 0.126 |
| MDA-N | 0.229 | 1.466 | 0.059 | 0.053 | 0.035 | 0.088 | 0.002 |
| BT-549 | 0.462 | 1.153 | 0.789 | 0.708 | 0.506 | 0.564 | 0.011 |
| T-47D | 0.439 | 1.300 | 0.739 | 0.671 | 0.653 | 0.603 | 0.057 |

FIG. 12E

"ANOLOG"
DATA SHEET

| | | | | | | | |
|---|---|---|---|---|---|---|---|
| 65 | 38 | 14 | 14 | -89 | 3.53E-08 | 1.38E-05 | 4.20E-05 |
| 70 | 44 | 28 | 50 | -76 | 5.88E-08 | 2.48E-05 | 6.18E-05 |
| 85 | 62 | 40 | 39 | -98 | 3.53E-07 | 1.93E-05 | 4.47E-05 |
| 95 | 71 | 36 | 1 | -98 | 4.04E-07 | 1.02E-05 | 3.27E-05 |
| 35 | 7 | -22 | -7 | -92 | <1.00E-08 | 1.69E-07 | 3.20E-05 |
| 31 | 23 | 21 | 18 | -99 | <1.00E-08 | 1.44E-05 | 3.84E-05 |
| 94 | 66 | 38 | 28 | -45 | 3.83E-07 | 2.40E-05 | >1.00E-04 |
| 100 | 87 | 43 | 27 | -100 | 6.88E-07 | 1.64E-05 | 4.06E-05 |
| 30 | 16 | 11 | 13 | -87 | <1.00E-08 | 1.34E-05 | 4.24E-05 |
| 22 | 8 | -6 | 3 | -75 | <1.00E-08 | | 4.79E-05 |
| -28 | -17 | -24 | -15 | -98 | <1.00E-08 | <1.00E-08 | 2.62E-05 |
| 110 | 96 | 82 | 25 | -77 | 3.66E-06 | 1.77E-05 | 5.48E-05 |
| 45 | 8 | -4 | -6 | -97 | <1.00E-08 | 4.78E-07 | 2.97E-05 |
| 8 | -12 | -21 | -19 | -29 | <1.00E-08 | 2.45E-08 | >1.00E-04 |
| -53 | -66 | -52 | -13 | -24 | <1.00E-08 | <1.00E-08 | <1.00E-08 |
| -74 | -77 | -85 | -62 | -100 | <1.00E-08 | <1.00E-08 | <1.00E-08 |
| 47 | 36 | 6 | 15 | -96 | <1.00E-08 | 1.35E-05 | 3.77E-05 |
| 35 | 27 | 25 | 19 | -87 | <1.00E-08 | 1.51E-05 | 4.48E-05 |

*FIG. 12F*

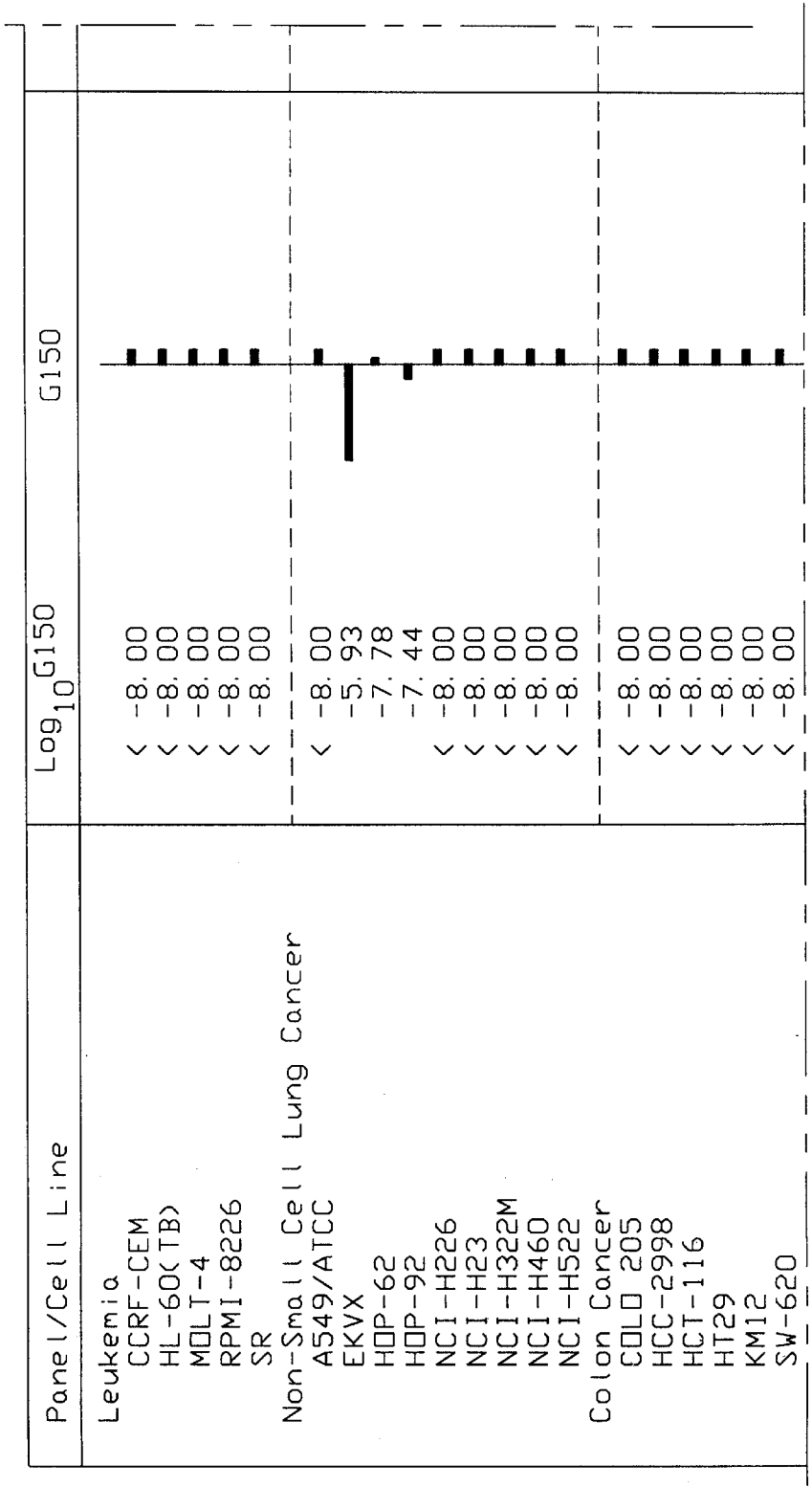

PREPARATION OF BROMINATED PACLITAXEL ANALOGUES AND THEIR USE AS EFFECTIVE ANTITUMOR AGENTS

STATEMENT OF RELATED APPLICATIONS

This application is a continuation in part of U.S. application Ser. No. 08/571,427, filed Dec. 13, 1995 now abandoned which is incorporated herein by reference.

FIELD OF THE INVENTION

This invention relates to paclitaxel analogues, namely diastereomers of 2", 3"-dibromocephalomannine and corresponding dibromo-7-epi-cephalomannine diastereomers; methods for their preparation, isolation, and purification; and their use as effective antitumor agents and alternatives to paclitaxel and paclitaxel derivatives.

BACKGROUND OF THE INVENTION

Cephalomannine is a natural product found in the bark of the Pacific yew tree *Taxus brevifolia*, and other yew species including *T. baccata, T. cuspidata, T. yunnanensis, T. chinensis, T. capitata, T. brownii*, and *T. dark green spreader*. It can also be found in Cephalotaxus species such as *Cephalotaxus mannii*, as well as cultured plant cells and fungi.

Cephalomannine is most often present in combination with its well known and structurally similar taxane paclitaxel. The structures of cephalomannine and paclitaxel are set forth below.

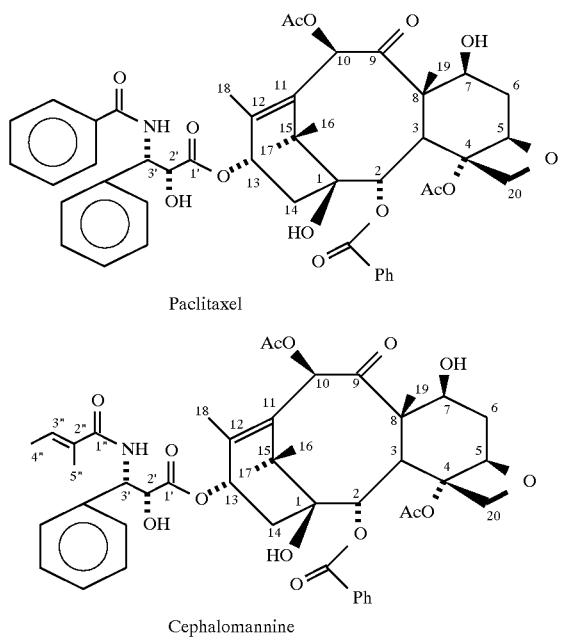

Paclitaxel

Cephalomannine

Paclitaxel has been approved by the Food and Drug Administration for treatment of ovarian and breast cancer. It is also presently undergoing clinical trials for treatment of other types of cancer. The natural supply of paclitaxel, however, is limited to a finite number of yew trees and other yew species containing relatively small amounts of paclitaxel. Therefore, alternate sources of paclitaxel as well as alternate compounds having paclitaxel-like antitumor activity are highly desired.

As set forth in U.S. Ser. No. 08/571,427, filed Dec. 13, 1995, which is incorporated herein by reference, a mixture of 2", 3"-dibromocephalomannine diastereomers has shown strong in vitro and in vivo paclitaxel-like efficacy in a variety of tumors, thereby providing a viable alternative to paclitaxel and paclitaxel derivatives such as Taxotere® (Rhône-Poulenc Rorer).

The chemical structures of both paclitaxel and cephalomannine contain eleven asymmetric carbon atoms, of which nine are in the taxane ring and two are in the side chain at carbon 13. Stereo-structures of cephalomannine and paclitaxel are shown below.

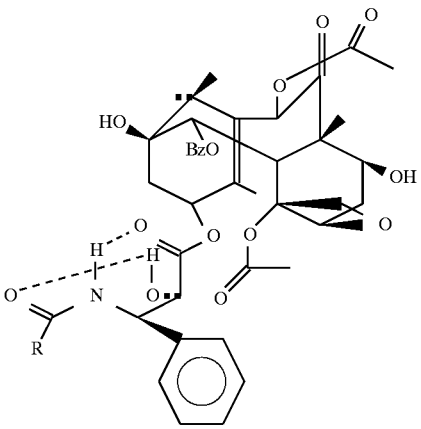

Stereoview of taxanes

1. Paclitaxel     R = 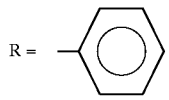

2. Cephalomannine;   R = 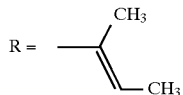

The cephalomannine structure contains a double bond in the side chain attached to carbon 13. This exocyclic double bond along with the number of stereocenters present in the structure of cephalomannine suggests the existence of numerous stereoisomers of this taxane. For example, cephalomannine can be distributed in two isomeric forms wherein the hydroxyl group at carbon 13 is acylated with phenylisoserine acylated in amino group by either (Z)- or (E)-2-methyl-2-butenoic acid leading to (Z)- and (E)-cephalomannines, respectively. In addition, it is known that cephallomannine and paclitaxel can be epimerized at carbon 7 either thermally, during chromatographic procedures, or in acidic or basic solutions. Miller, et al.,*J. Org. Chem.*, 46:1469 (1981); Chaudhary, et al. *J. Org. Chem.*, 58:3978 (1993) and Wender, et al., CRC Press, Inc., Boca Raton, Fla., (1995) p.130. Thus, during halogenation, each of these isomers can give rise to a mixture of diastereomeric products.

In accordance with this invention, individual diastereomers of 2", 3"-dibromocephalomannine and the corresponding dibromo-7-epi-cephalomannine diastereomers have been isolated and purified. Most likely, the 7-epi-cephalomannine is produced from cephalomannine during isolation and purification procedures. The mixture of the diastereomers shows strong in vitro and in vivo paclitaxel-like antitumor activity.

SUMMARY OF THE INVENTION

The present invention provides novel selectively brominated derivatives of cephalomannine and 7-epicephalomannine having in vitro and in vivo paclitaxel-like antitumor activity, methods of preparation therefor as well as methods for treating tumors with these compounds. The brominated stereospecific cephalomannine derivatives of this invention are prepared in good yields from either complex mixtures comprising cephalomannine, paclitaxel, and other taxane compounds, or from more refined sources of cephalomannine by selective bromination of the unsaturated 2", 3" side-chain of the cephalomannine molecule while leaving other parts of the molecule or other important taxane components in the mixture, such as paclitaxel, intact. Thus, bromination of cephalomannine/7-epi-cephalomannine produces 2", 3"-dibromo diastereomers of each which are easily separated from the mixture by chromatographic procedures, which show strong antitumor efficacy. This invention is more fully described by the following detailed description of preferred embodiments and drawings.

DETAILED DESCRIPTION OF PREFERRED EMBODIMENTS

Figure 1A:
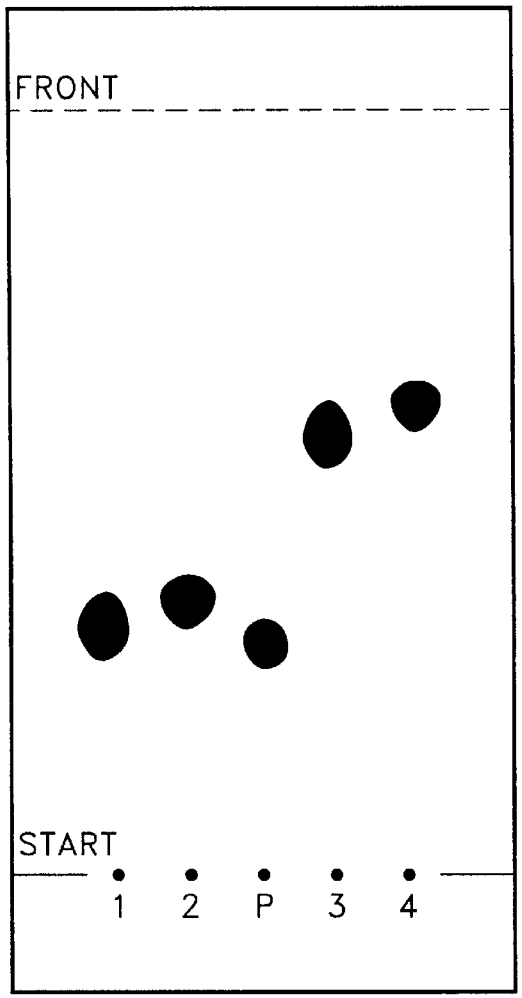
FIG. 1 is a TLC separation of dibromocephalomannine and dibromo-7-epi-cephallomannine diastereomers (DiBr-I-IV).

The present invention provides for the preparation, isolation and purification of 2", 3"-dibromocephalomannine and 2", 3"-dibromo-7-epi-cephalomannine diastereomers from unpurified, partially purified or purified mixtures of cephalomannine, 7-epi-cephalomannine, paclitaxel and other taxanes by reacting the mixture with bromine under conditions inclusive of a temperature and for a time effective to selectively brominate the unsaturated 2", 3" side-chain portion of cephalomannine and 7-epi-cephalomannine present, and then separating the resulting less polar dibromocephalomannine and dibromo-7-epi-cephalomannine diastereomers from paclitaxel and other taxane compounds and isolating and purifying individual diastereomers thereof by standard chromatographic techniques and/or crystallization.

The method of the present invention is advantageously independent of the concentration of cephalomannine and 7-epi-cephalomannine present in various complex mixtures of taxane compounds, and can utilize any source containing cephalomannine and 7-epi-cephalomannine as starting material. These sources include the bark from various Taxus species including *Taxus brevifolia, Taxus baccata, Taxus yunnanensis, Taxus chinenesis* and *Taxus wallichiana*, from Cephalotaxus species such as *Cephalotaxus mannii* plant material such as needles and twigs from various Taxus and Cephalotaxus species, extracts of biomass containing a complex mixture of taxane type compounds, as well as in the downstream purification of cephalomannine and 7-epi-cephalomannine produced from sources such as cell cultures of Taxus and Cephalotaxus species and cephalomannine and 7-epi-cephalomannine producing fungi.

In a preferred method of the present invention, a mixture of taxanes, comprising cephalomannine and/or 7-epi-cephalomannine and paclitaxel, is treated with stoichiometric quantities of bromine dissolved in an inert solvent, preferably carbon tetrachloride, chloroform, methylene chloride, or ethylene dichloride. In a typical treatment, a mixture containing approximately 30% by weight cephalomannine with bromine in carbon tetrachloride results in a quantitative yield of a mixture of 2", 3"-dibromocephalomannine diastereomers and the corresponding 7-epi-cephalomannine diastereomers. See Scheme I.

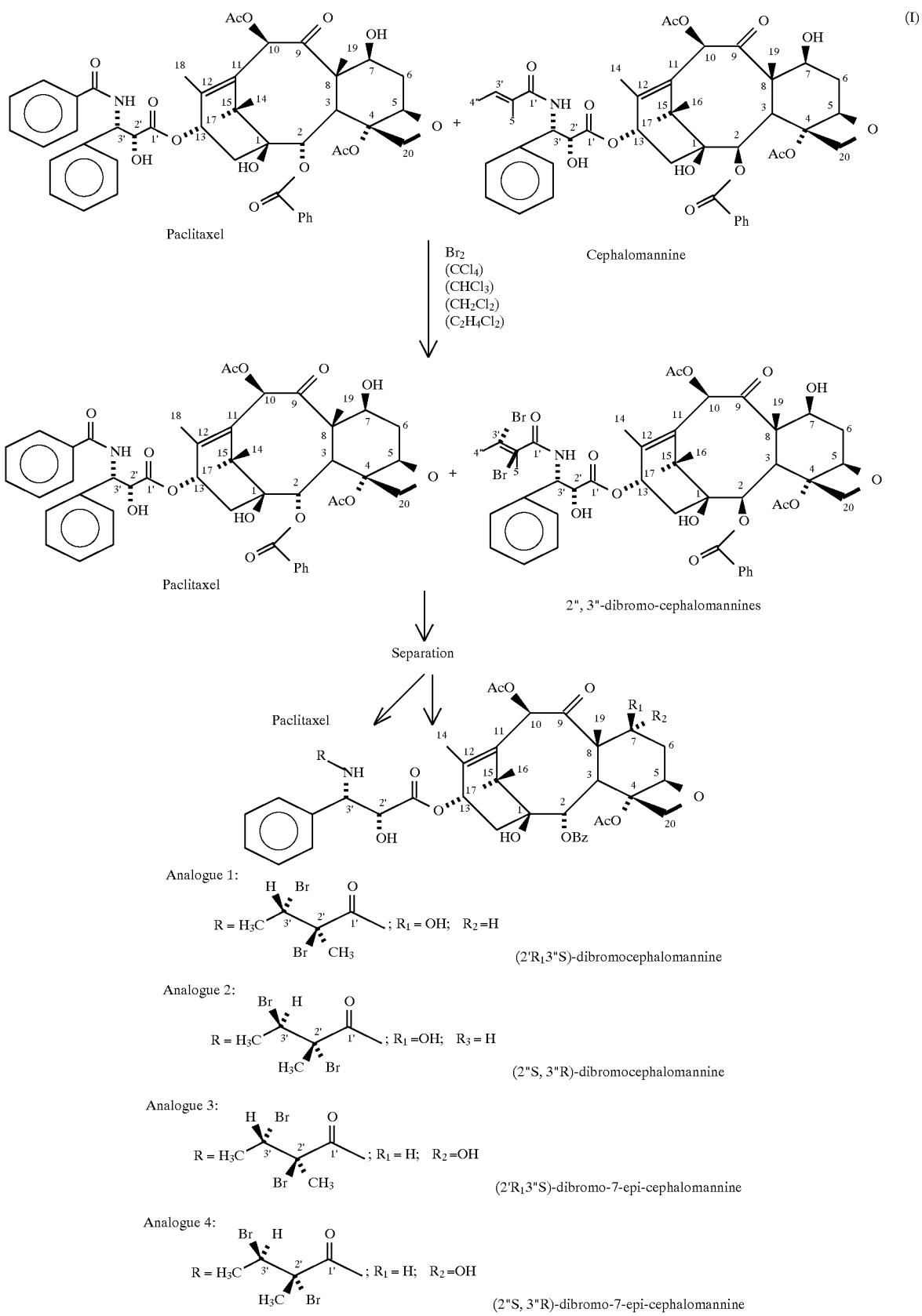

The resulting diastereomers can be separated and their chemical structures elucidated using modern physicochemical methods (m.p., TLC, HPLC, UV, IR, NMR, MS).

For mixtures containing cephalomannine and from about 0.01% to about 99.5% paclitaxel, the process is similar to that described above. The mixture is first dissolved in an inert solvent, preferably carbon tetrachloride, chloroform, 1,2-dichloroethane or methylene chloride. To this solution is added a solution of bromine in carbon tetrachloride, and the mixture stirred until the cephalomannine is completely reacted. Cephalomannine and 7-epi-cephalomannine are brominated with high selectivity to diastereomers of 2", 3"-dibromocephalomannine and 2", 3"-dibromo-7-epi-cephalomannine, respectively. The progress of reaction can be conveniently monitored, for example, by HPLC analysis. The resulting mixture containing other taxane impurities can be separated and purified using conventional methods such as chromatography and crystallization.

The molar equivalents of bromine used is dependent on the cephalomannine and 7-epi-cephalomannine content and presence or absence of other unsaturated compounds. Generally, a less pure mixture, for example, a mixture containing large amounts of unsaturated taxanes relative to cephalomannine and 7-epi-cephalomannine, requires higher molar equivalents of bromine to substantially completely brominate all the cephalomannine and 7-epi-cephalomannine present in the mixture. Structures are shown below of other unsaturated taxanes which are typically present along with cephalomannine, 7-epi-cephalomannine and paclitaxel in plant extracts.

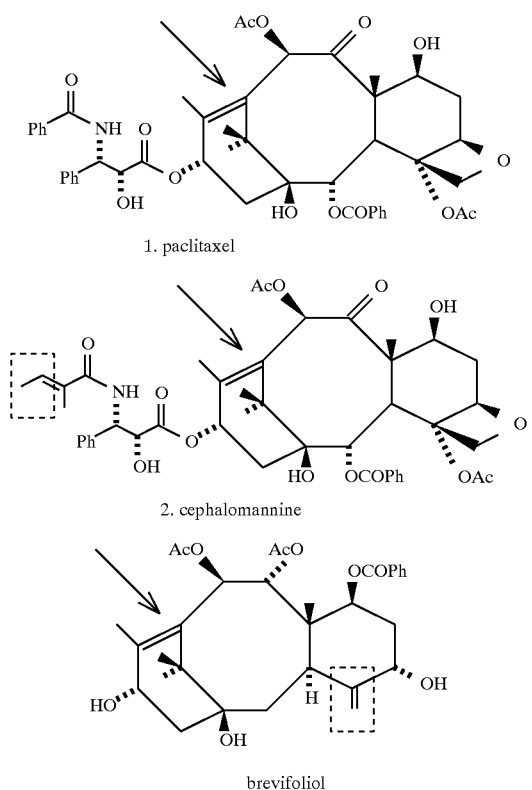

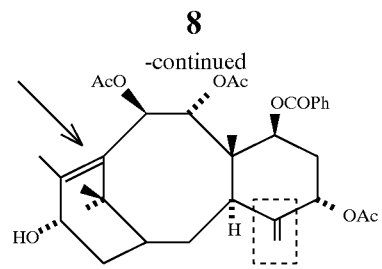

taxusin

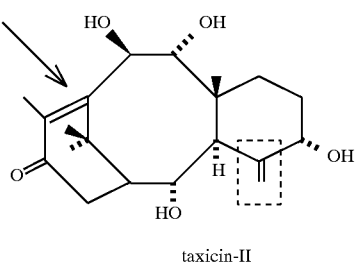

taxicin-II

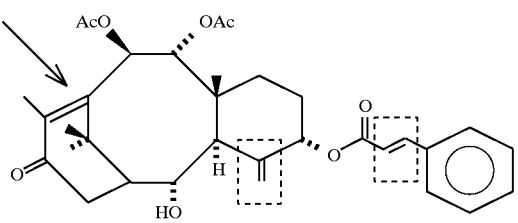

taxicin-I

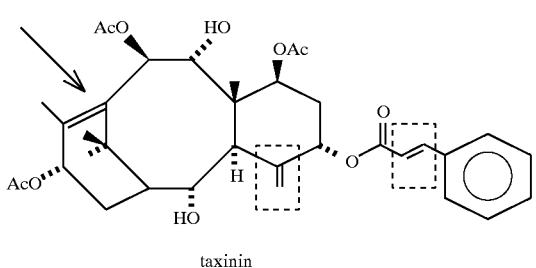

taxinin

The solvents used for bromination in this invention should be inert to bromine. As mentioned hereinabove, the most useful and preferred solvents are chlorinated solvents, such as carbon tetrachloride, chloroform, 1,2-dichloroethane, and methylene chloride. The bromination process is most effective within about −20° C. to about 20° C. when run in the dark, and it is highly preferred that the reaction temperature be maintained between about −5° and about 5° C. The preferred source of bromine is in carbon tetrachloride solution from 0.01M to 0.1M.

Conventional wisdom would lead one to expect that the use of bromine in the presence of taxane compounds having several functional groups would result in undesired side reactions and deplete the concentration of cephalomannine and/or 7-epi-cephalomannine and bromine without generating the desired dibromocephalomannines or appreciable yields thereof. However, in accordance with this invention, it has been found that selectivity for bromination of 2", 3"-double bond in cephalomannine and 7-epi-cephalomannine is very high under controlled conditions. In this inventive process, paclitaxel is neither significantly degraded nor brominated during the reaction. Further, any undesired degradation during bromination can be avoided and the proper conditions adjusted appropriately without undue experimentation by periodically monitoring the reaction, for example, by HPLC analysis.

The following examples are provided to illustrate preferred embodiments for selective bromination of samples containing cephalomannine, 7-epi-cephalomannine, paclitaxel and other taxanes in different ratios, without significant undesired degradation, for example, of paclitaxel. It is to be understood, however, that these examples are only intended to illustrate some preferred embodiments of the invention, and are in no way intended to limit the scope or spirit of the invention as defined in the claims.

EXPERIMENTAL

Raw Materials

Batches of crude plant extracts from *Taxus yunnanensis* having approximately 15–40% cephalomannine, 50–70% paclitaxel, and approximately 20–35% other taxane/non-taxane components were obtained from the Peoples Republic of China. Bromine reagent was obtained from Fisher Scientific. Silica gel used was ICN Silitech, 32–63 um, 60 Å, ICN Biomedicals, Inc., Aurora, Ohio. All solvents used were either HPLC or ACS grade and were obtained from Spectrum Chemical Mfg. Corp. Purified water used was deionized in-house.

EXAMPLE I

Bromination of Crude Plant Extract

Crude plant extract (10.0 g, 26.4% cephalomannine) was dissolved in chloroform so that a total of 250 ml solution was obtained. To the solution cooled in an ice bath and continually stirred with a magnetic stirrer was added carbon tetrachloride (4750 ml). To the cooled solution (4° C.) was added dropwise 0.1M bromine in carbon tetrachloride (40 ml). HPLC analysis of this mixture indicated a ratio of paclitaxel to cephalomannine peak areas 2.6 to 1. The reaction mixture was stirred in the dark with the temperature gradually rising to 15° C. After 7 hrs of reaction, an additional 7 ml 0.1M bromine in carbon tetrachloride was added and the reaction continued overnight (14 hrs). HPLC analysis of the mixture showed a ratio of paclitaxel to cephalomannine peak areas 6.5 to 1. An additional 7 ml 0.1M bromine in carbon tetrachloride was added and the reaction continued at 15° C. After an additional 8 hrs of reaction, the final portion of 7 ml of 0.1M bromine in carbon tetrachloride was added and the reaction continued at 15° C. overnight (14 hrs). Subsequent HPLC analysis of the mixture showed a ratio of paclitaxel to cephalomannine peak areas of 11:1. This ratio increased to 12.3:1 after another 7 hrs of reaction. The mixture was then washed with 5 l 0.2% aqueous sodium sulfite solution. The pH of the aqueous layer was 8.0. This was followed by two washes with water (2×5 l).

The pH of first and second water washes were 6.5–7.0 and 6.0–6.5 respectively. The combined aqueous layer was reextracted with 5 l chloroform. The organic layers were combined, dried with anhydrous sodium sulfate (500 g), and evaporated to dryness using a rotary vacuum evaporator at 40° C.

The solid residue (13.64 g) was purified by chromatography.

EXAMPLE II

Chromatographic Purification of Brominated Material

The thus obtained brominated material (13.64 g) was purified by medium pressure chromatography using a column (6.9 cm i.d., 70 cm long) packed with silica gel (ICN Silitech, 32–63 um, 60 Å) by the slurry method using 1.5% methanol in 1,2-dichloroethane. The sample dissolved in the same solvent was loaded and eluted at the rate of 50 ml/min. Total 55 fractions (500 ml each) were collected. The fractions were analyzed by TLC. The TLC-plates were developed with 10% methanol in 1,2-dichloroethane and detected with 1% vanillin in 50/50 sulfuric acid-methanol. Dibromo-7-epi-cephalomannines eluted in fractions 10–14 and yielded 1.42 g solids following evaporation of solvents. Likewise, the dibromocephalomannines eluted in fractions 24–28 and yielded 1.64 g solids following evaporation of solvents. Individual diastereomers of dibromocephalomannine and the corresponding 7-epi-cephalomannine were subsequently separated and isolated by semi-preparative HPLC discussed below.

Evaporation of medium pressure chromatographic fractions 34–54 yielded 4.79 g of paclitaxel, m.p. 214°–216° C., with analytical data obtained from HPLC, UV, IR, MS, NMR the same as presented in U.S. Ser. No. 08/571,427.

EXAMPLE III

Separation of 2", 3"-dibromocephalomannine and 2", 3"-dibromo-7-epi-cephalomannine diastereomers The final purification of dibromocephalomannine and dibromo-7-epi-cephalomannine diastereomers from other impurities was accomplished by semi-preparative HPLC (Waters Deltaprep 3000) using a Waters Deltapak C18 column, 100 Å, 19 mm×30 cm with 50% acetonitrile in water as the mobile phase at a flow rate of 15 ml/min. Peak elution was monitored using a UV detector (Waters Lambda-Max Model 481) set at 227 nm. Portions of 200 mg of material dissolved in methanol (2 ml) were injected into the column. Elution of dibromocephalomannine diastereomer I peaked approximately at 54 min. and diastereomer II at 56 min. Likewise, the dibromo-7-epi-cephalomannine diastereomer III peaked at approximately 104 min. and the corresponding diastereomer IV peaked at 112 min. respectively. Fractions collected from repeated injections were pooled and evaporated at 40° C. under reduced pressure to remove the organic solvent. The crystallized solids were filtered, washed with water, and dried in a vacuum oven at 40° C. to yield pure dibromocephalomannine and dibromo-7-epi-cephalomannine diastereomers. The separation and structures of the four diastereomeric dibromo compounds of this invention, (I): (2"R, 3"S) -dibromocephalomannine, (DiBr-I)

(II): (2"S, 3"R) -dibromocephalomannine, (DiBr-II)

(III): (2"R, 3"S) -dibromo-7-epi-cephalomannine, DiBr-III and (IV): (2"S, 3"R) -dibromo-7-epi-cephalomannine, (DiBr-IV)

are set out below in Scheme II:

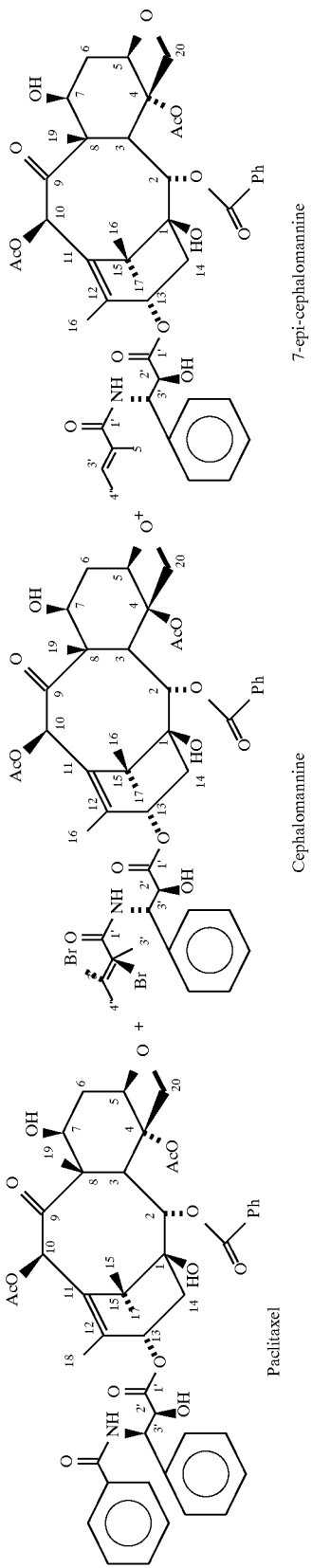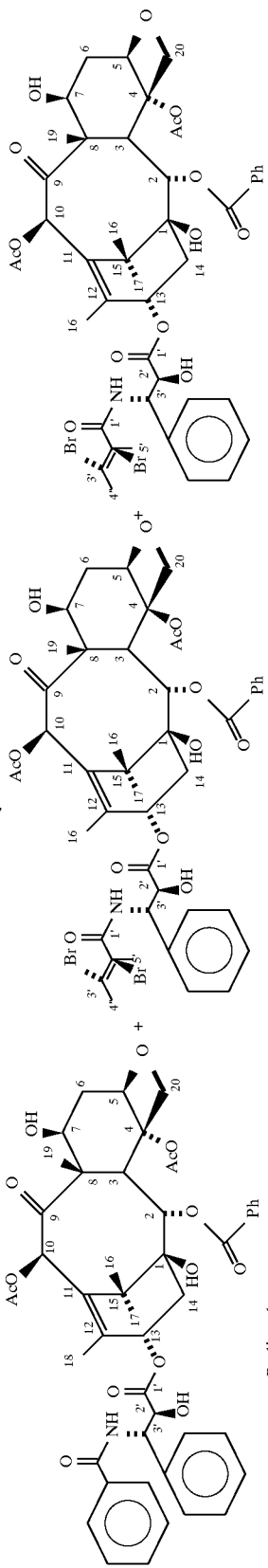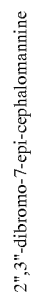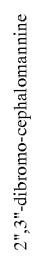

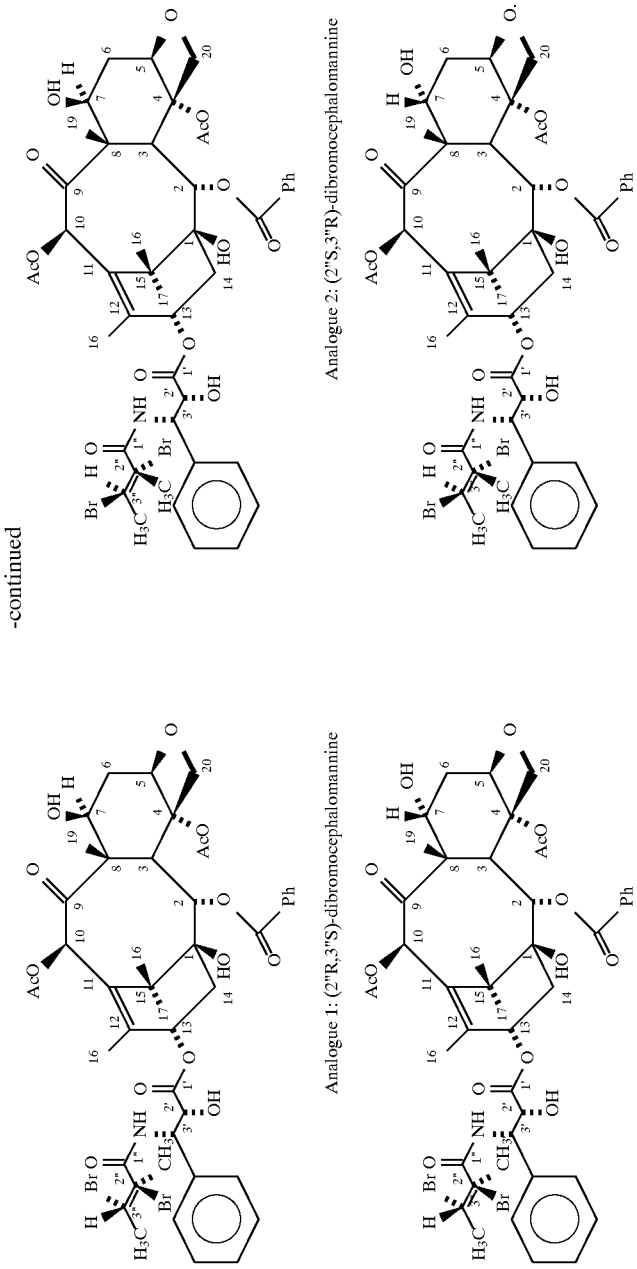

PACLITAXEL ANALOGUES (BROMINATED)

Figure 1B:
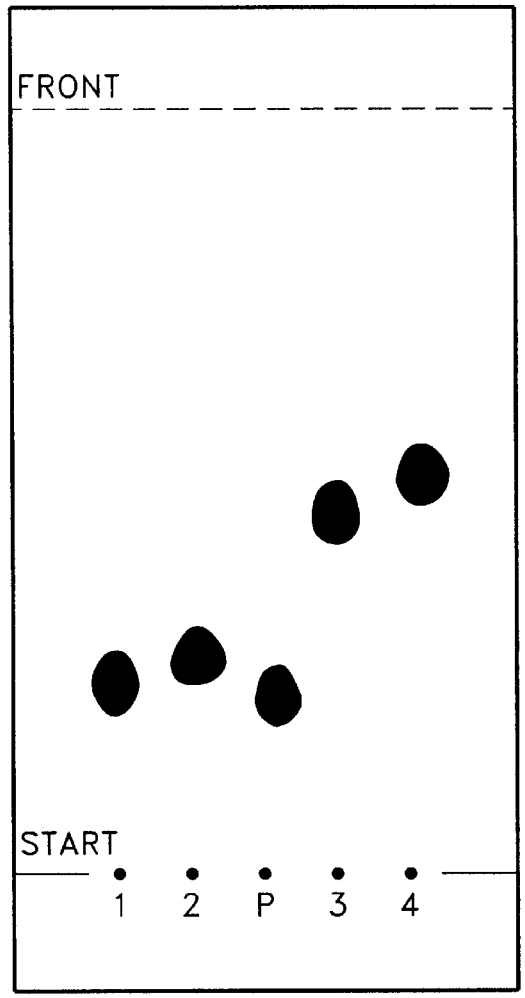

Analysis of the diastereomers of this invention is as follows:

FIG. 1 is a TLC separation of 2", 3"-dibromocephalomannine and 2", 3"-dibromo-7-epi-cephalomannine diastereomers (DiBr-I-IV) as summarized below in Table 1.

TABLE 1

| lane | Compound | |
|---|---|---|
| (1) (DiBr-I) | (2"R, 3"S)-dibromocephalomannine | |
| (2) (DiBr-II) | (2"S, 3"R)-dibromocephalomannine | |
| (6) (DiBr-III) | (2"R, 3"S)-dibromo-7-epicephalomannine | |
| (7) (DiBr-IV) | (2"S, 3"R)-dibromo-7-epicephalomannine | |
| (T) paclitaxel | | |
| plate: | silicagel 60 $F_{254}$ (Merck #5554) | |
| solvent system: | a) | 10% $CH_3OH$ in 1,2-dichloroethane |
| | b) | hexane/chloroform/EtOAc/$CH_3OH$ 20/60/15/5 |
| reagent: | a) | UV light |
| | b) | Vanilin/$H_2SO_4$ in methanol |

Figure 2:
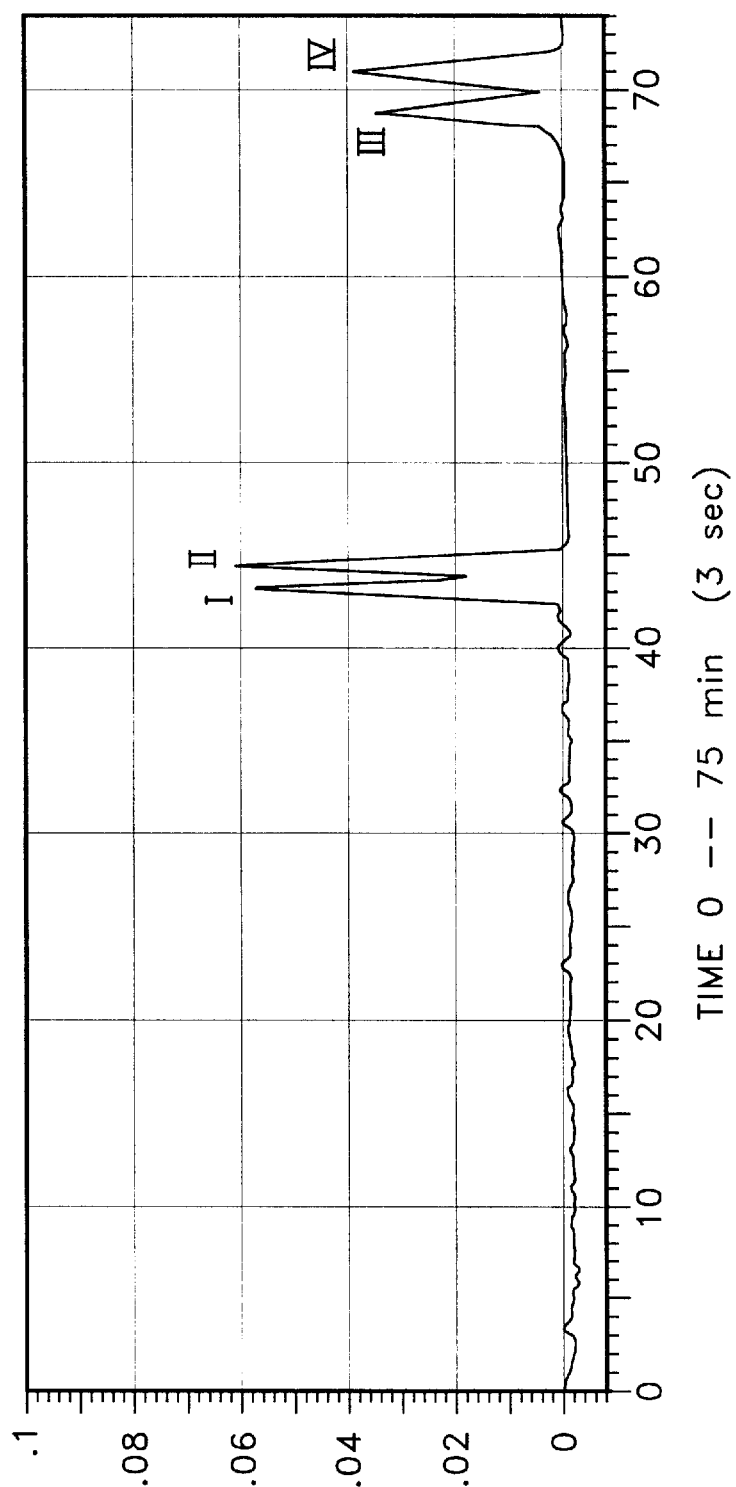
FIG. 2 is a HPLC chromatogram of dibromocephalomannine diastereomers and dibromo-7-epi-cephalomannine diastereomers.

FIG. 2 is a HPLC chromatogram of a mixture of diastereomers (I) DiBr-I; (II)DiBr-II; (III)DiBr-III; and (IV)DiBr-IV. Equipment and conditions employed in generating this chromatogram are the following:

Column: ES Industries FSP (pentafluorophenyl) 4.6 mm ID×250 mm, 5 um particle size, 60 Å pore size Solvent System: water/acetonitrile/methanol, 41:39:20

Flow Rate: 0.50 ml/min., isocratic

Detector: Waters 990 photodiode array detector, monitored at 227 nm

Injection Volume: 20 ul

Figure 3:
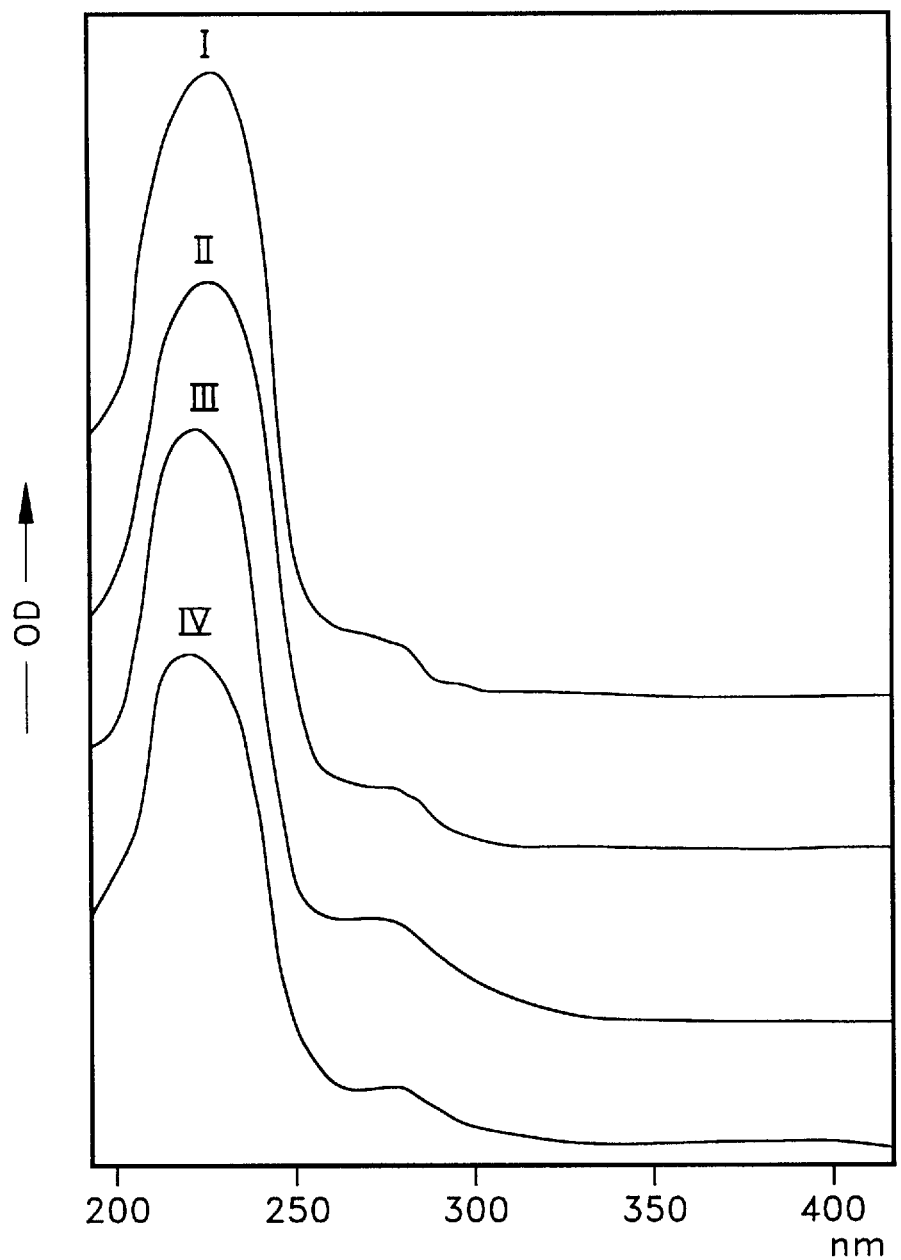
FIG. 3 shows a comparison of the UV spectra of pure dibromocephalomannine and pure dibromo-7-epi-cephalomannine diastereomers.

FIG. 3 are superimposed UV spectra of pure diastereomers DiBr-I, DiBr-II, DiBr-III and DiBr-IV in $CH_3OH$. The spectra are summarized below in Table 2.

TABLE 2

| ISOMER | λ max (nm) | (ε) |
|---|---|---|
| DiBr-I | 226.0 | 14,732 |
| DiBr-II | 226.0 | 12,415 |
| DiBr-III | 219.4 | 37,900 |
| DiBr-IV | 218.4 | 20,013 |

Figure 4:
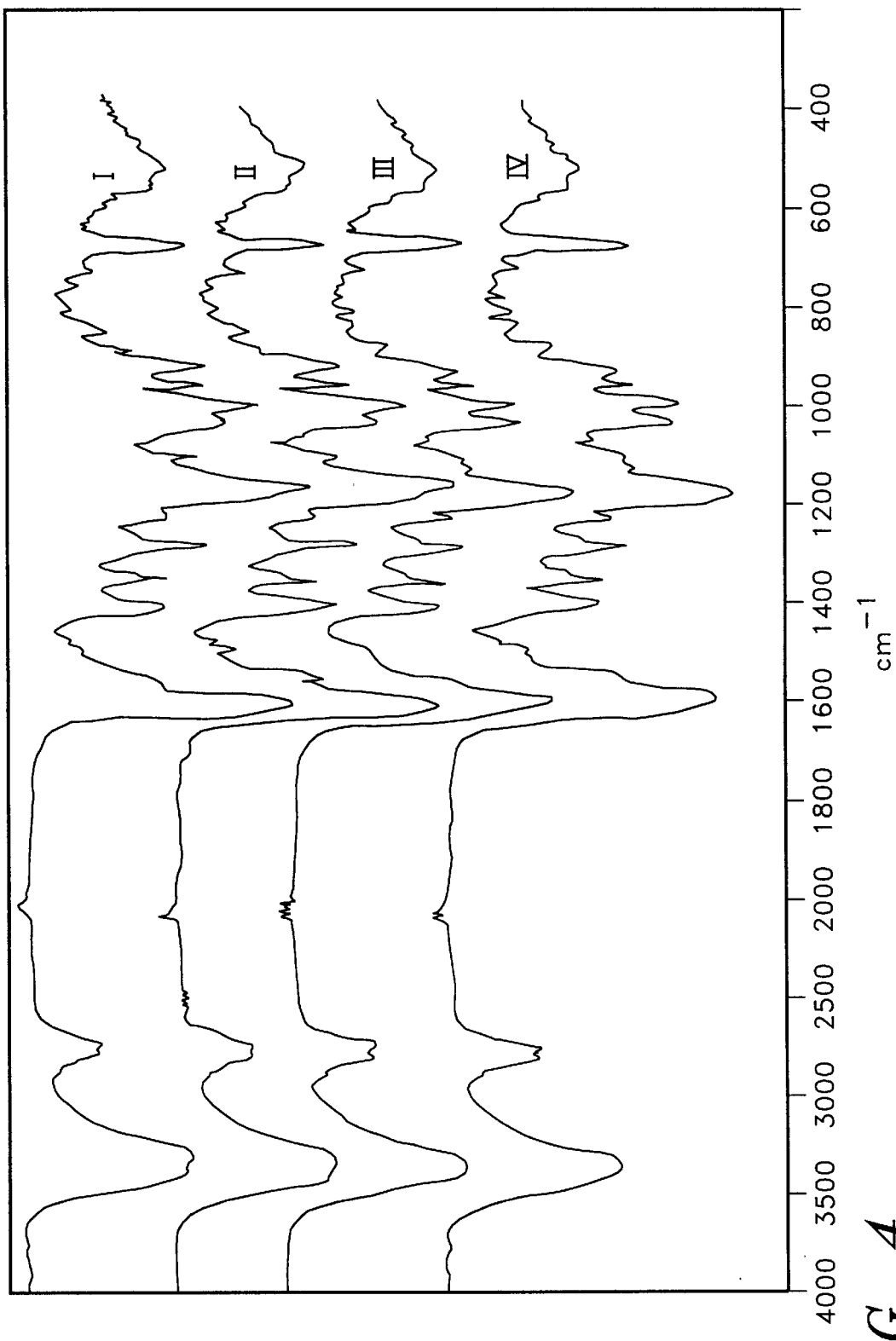
FIG. 4 shows a comparison of the IR spectra of pure dibromocephalomannine and dibromo-7-epi-cephalomannine diastereomers.

FIG. 4 are superimposed IR spectra of diastereomers DiBr-I, DiBr-II, DiBr-III and DiBr-IV in KBr, which spectra are summarized below in Table 3.

TABLE 3

| Band, cm$^{-1}$ | Functional Groups |
|---|---|
| 3500, 1105, 1070 | tert. and sec. OH |
| 3420, 1670, 1580 | —CONH— |
| 3110, 3060, 1605 | monosubs. aromatic |
| 1505, 770, 710 | rings |
| 2960, 2915, 2870 | —$CH_3$—; —$CH_2$—; —CH— in |
| 1465, 1370 | aliphatic or cylic comps. |
| 3020, 1670, 1310 | double bonds |
| 980 | |
| 730, 1270 | aromatic esters |
| 1715, 1240 | >c = o |
| 1730, 1180 | acetates |
| 855 | oxethane ring |

Figure 5:
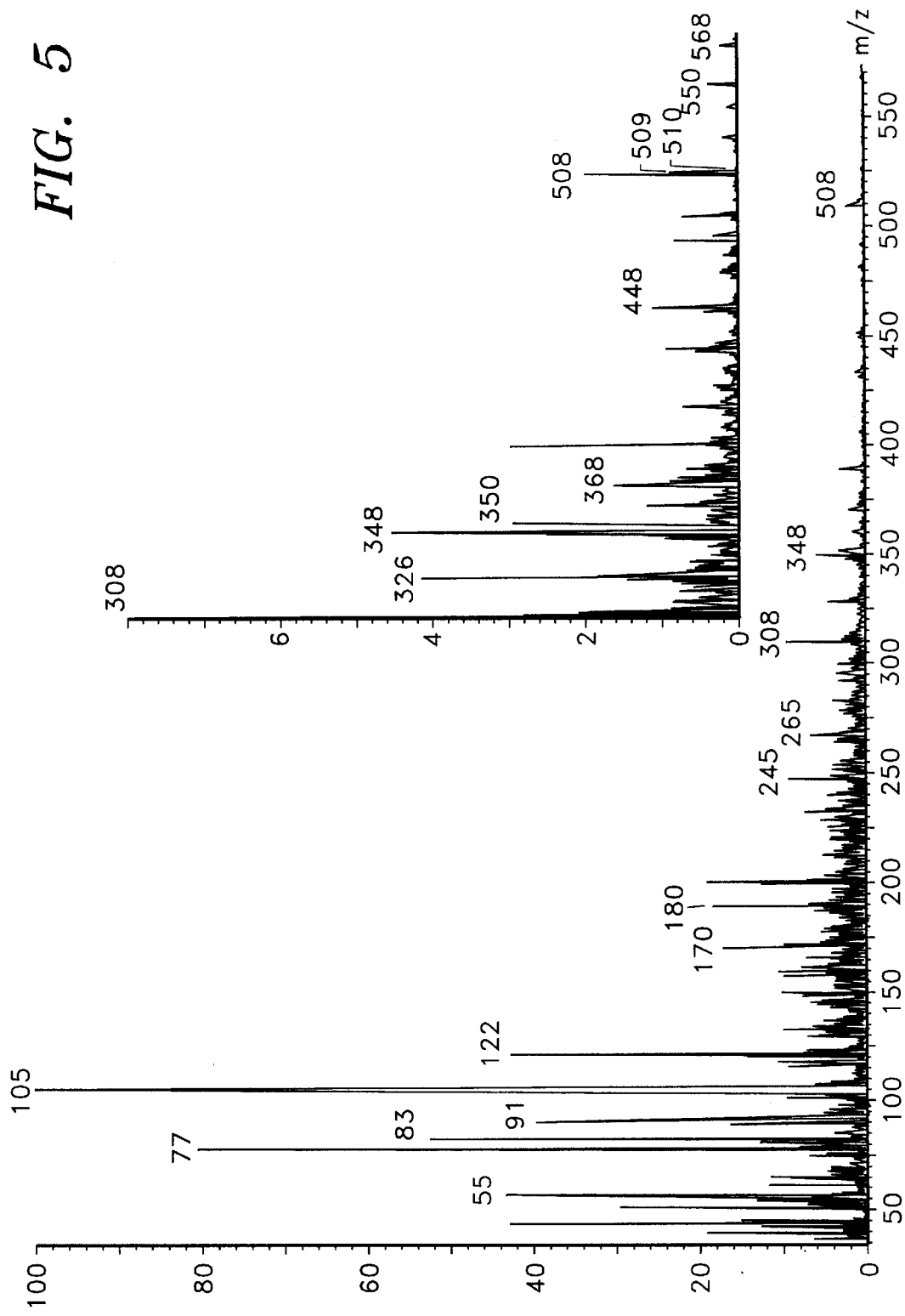
FIG. 5 is an EI-MS spectrum of (2"R,3"S) dibromocephalomannine (I) which is the same fragmentation pattern for other dibromocephalomannine and dibromo-7-epi-cephalomannine diastereomers.
Figure 6:
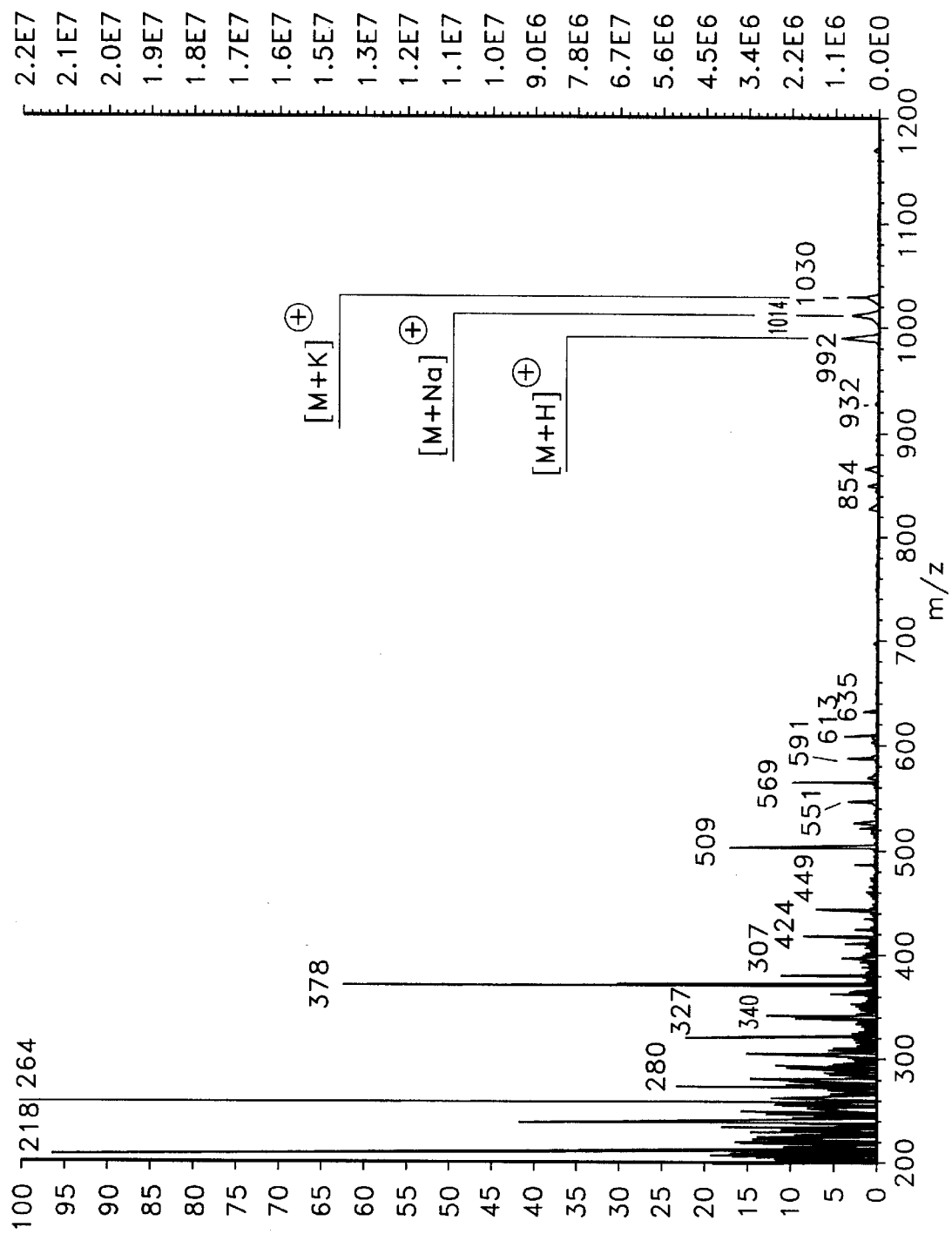
FIG. 6 is a FAB$^+$ spectrum of (2"R,3"S) dibromocephalomannine (I) which is the same fragmentation pattern for other dibromocephalomannine and dibromo-7-epi-cephalomannine diastereomers.
Figure 7:
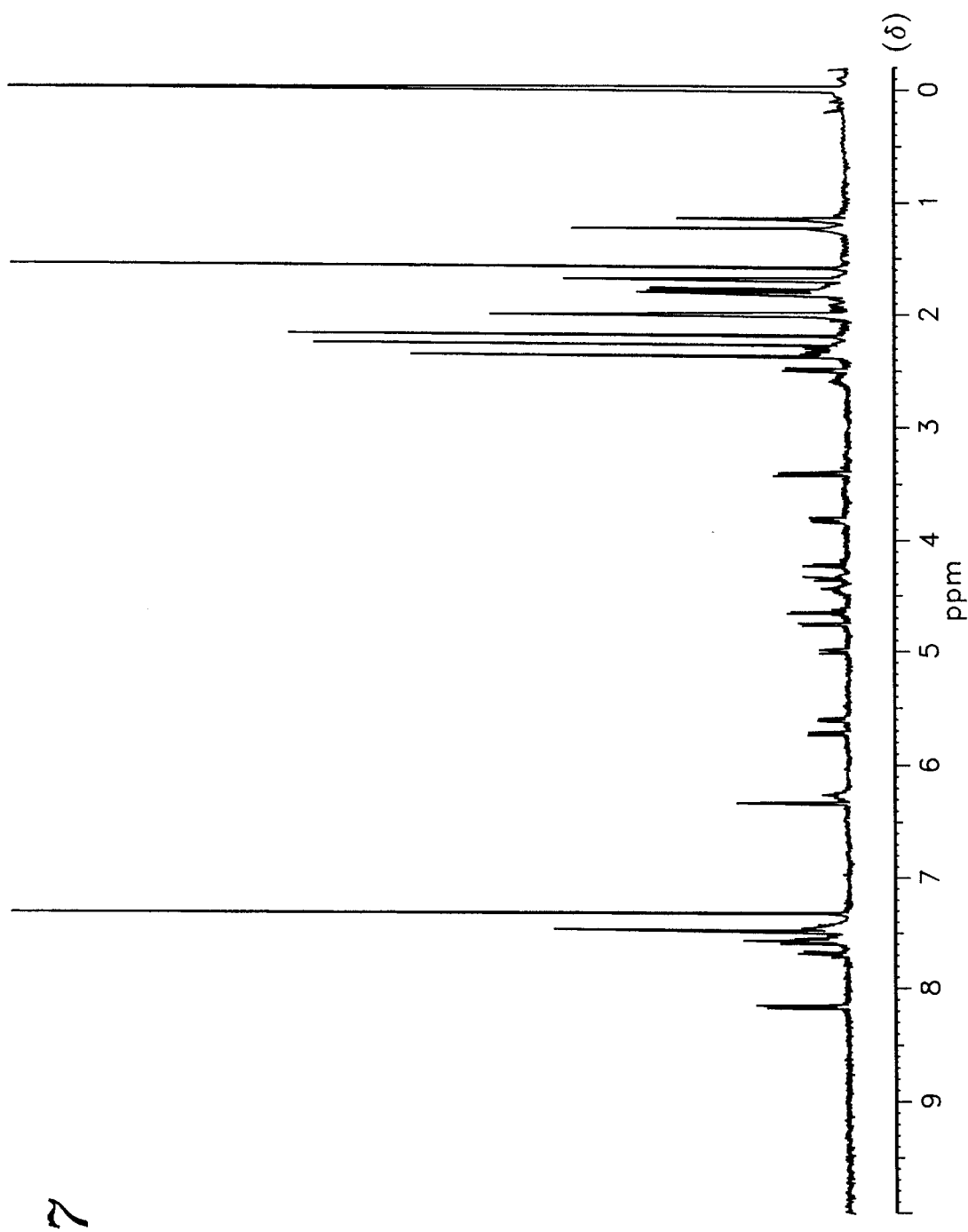
FIG. 7 is an $^1$H-NMR spectra of pure (2"R,3"S) dibromocephalomannine diastereomer(I).
Figure 8:
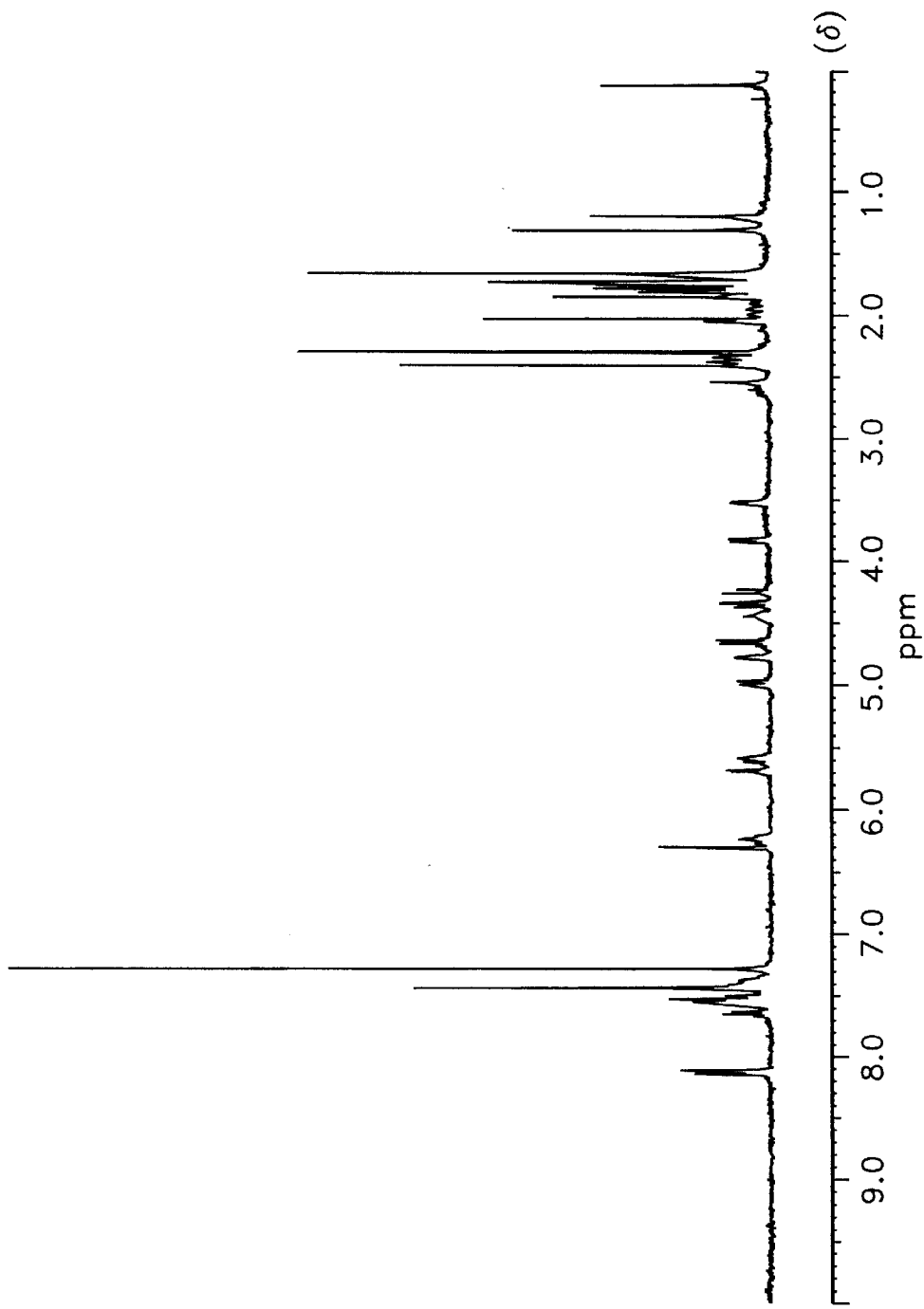
FIG. 8 is an $^1$H-NMR spectra of pure (2"S,3"R) dibromocephalomannine diastereomer (II).
Figure 9:
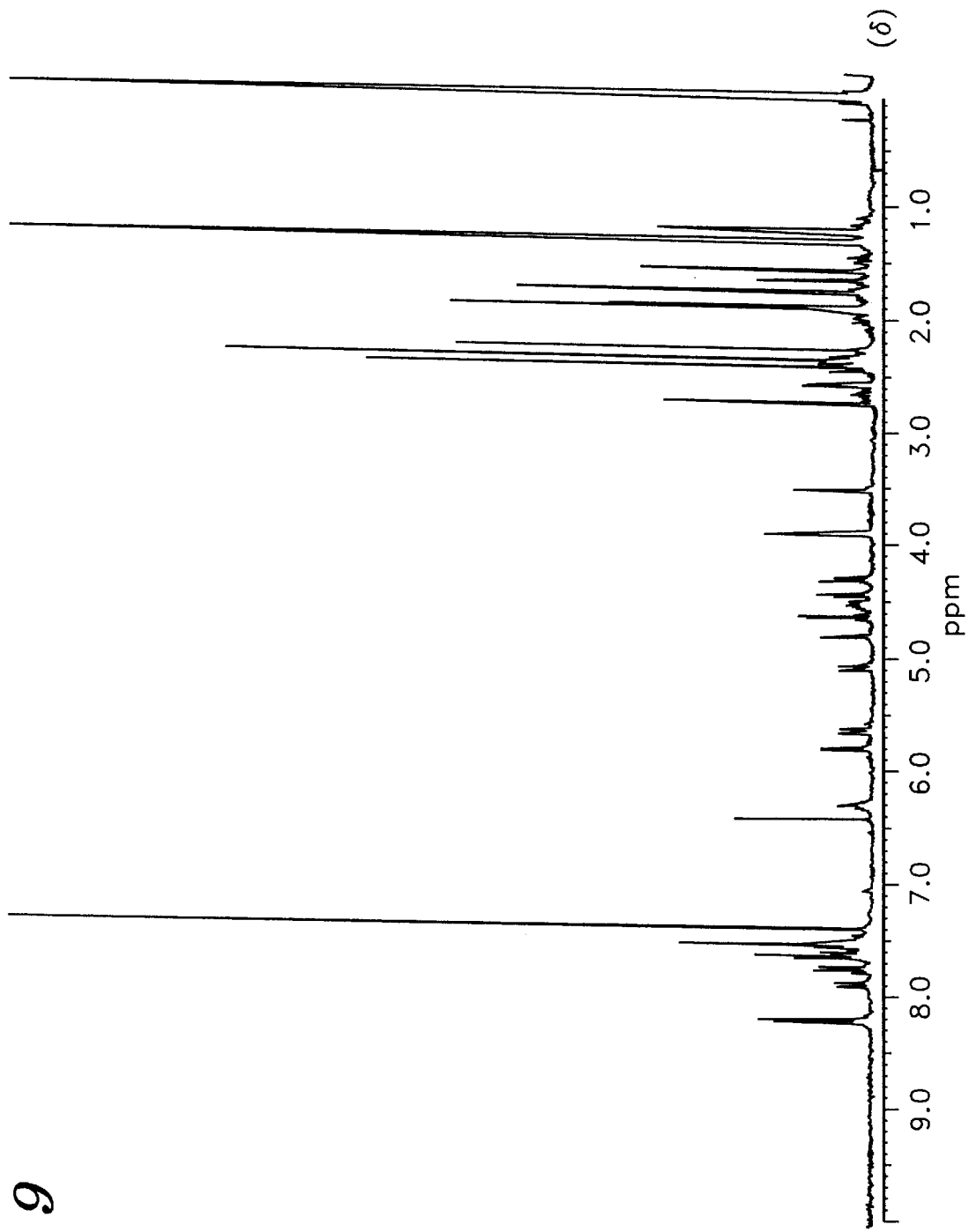
FIG. 9 is respective $^1$H-NMR spectra of pure (2"R,3"S) dibromo-7-epi-cephalomannine diastereomer (III).
Figure 10:
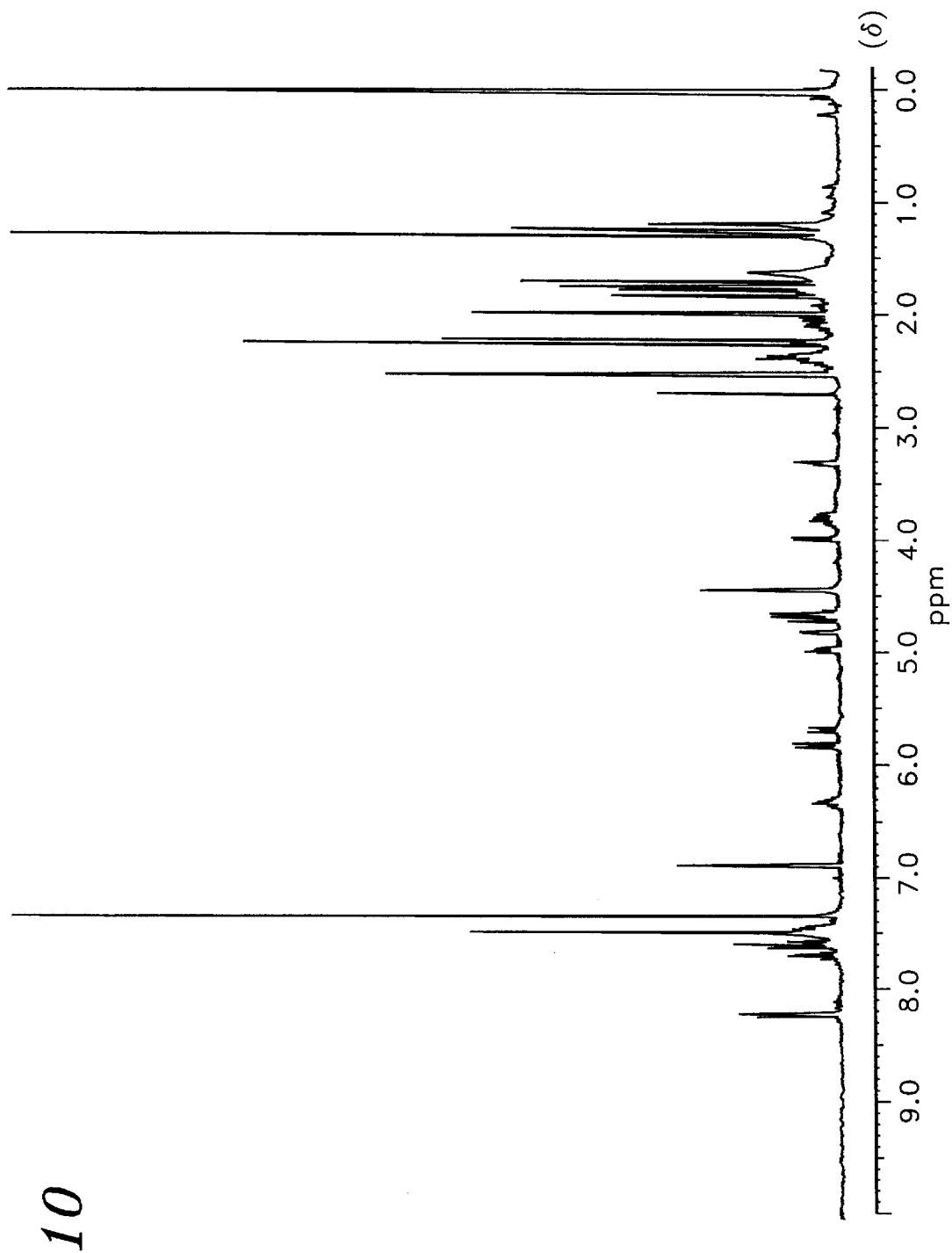
FIG. 10 is respective $^1$H-NMR spectra of pure (2"S,3"R) dibromo-7-epi-cephalomannine diastereomer (IV).

FIGS. 5 and 6 are respective EI-MS FAB$^+$-MS mass spectra of respective diastereomers DiBr-I; DiBr-II; DiBr-III and DiBr-IV, all of which have the same fragmentation pattern, and which are summarized below.

FIG. 5 EI-MS of DiBr-I, DiBr-II, DiBr-III and DiBr-IV; [M]$^+$=992 (m/z; the main fragments)

568 [T]$^+$; 550 [T–$H_2O$]$^+$; 508 [T–AcOH]$^+$;

490 [T–AcOH–$H_2O$]$^+$; 448 [T–2AcOH]$^+$;

or [T–BzOH]$^+$; 390 [S—O—$H_2O$]$^+$;

386 [T–AcOH–BzOH]$^+$; 348 [S—O—CO—HCHO]$^+$;

326 [T–BzOH–2 AcOH]$^+$; 308 [T–326–$H_2O$]$^+$;

284 [327–Ac]$^+$; 264 [832–T]$^+$; or

[424–2HBr]$^+$; 246 [264–$H_2O$]$^+$;

218 [264–HCOOH]$^+$; 188, 167 [S—$C_5H_8ONBr_2$]$^+$;

148 [167–$H_2O$]$^+$; 122 [BzOH]$^+$; 105 [Bz]$^+$;

91 [$C_7H_7$]$^+$; 83 [$C_4H_7C\equiv O$]$^+$; 77 [$C_6H_5$]$^+$; 57,55.

(T=taxane ring in the compound;

S=acid (side) chain in the compound.)

FIG. 6 FAB$^+$ - MS DiBr-I, DiBr-II, DiBr-III and DiBr-IV: (positive ion mode) (m/z)

1030 [M+K]$^+$; 1014 [M+Na]$^+$; 992 [M+H]$^+$ (See Elem. Anal.); 974 [M–$H_2O$]$^+$; 932 [M–AcOH]$^+$;

914 [M–AcOH–$H_2O$]$^+$; 912 [M–HBr]$^+$; 870 [M–BzOH]$^+$; 854 [870–$H_2O$–2H]; 832 [M–2HBr]$^+$;

705 [M–243–Ac]$^+$; 569 [T]$^+$; 551 [T–$H_2O$];

509 [T–AcOH]$^+$; 491[T–AcOH—$H_2O$]$^+$; 448[T–BzOH]$^+$;

429; 424 [$SH_2$]$^+$; 413; 405[S—$H_2O$]$^+$; 391 [S—O—$H_2O$]$^+$; 387 [T–AcOH–BzOH]$^+$; 376; [SBr—$CO_2$–2H$^+$]347 [S—O—CO—HCHO]$^+$; 338:327 [387–T–AcOH]$^+$; 315; 284[327–Ac]$^+$, 279; 264[832–T]$^+$ or

[424–2HBr]$^+$; 246[264–$H_2O$]$^+$; 231; 218[264–HCOOH]$^+$;

188; 167[S—$C_5H_8ONBr_2$]$^+$; 149[167–$H_2O$]$^+$;

133; 122[BzOH]$^+$; 113:105[Bz]$^+$; 91[$C_7H_7$]$^+$;

83; 77 [$C_6H_5$]$^+$; 76; 57; 55;

(T=taxane ring in the compound; S-acid (side) chain in the compound.)

Figure 11:
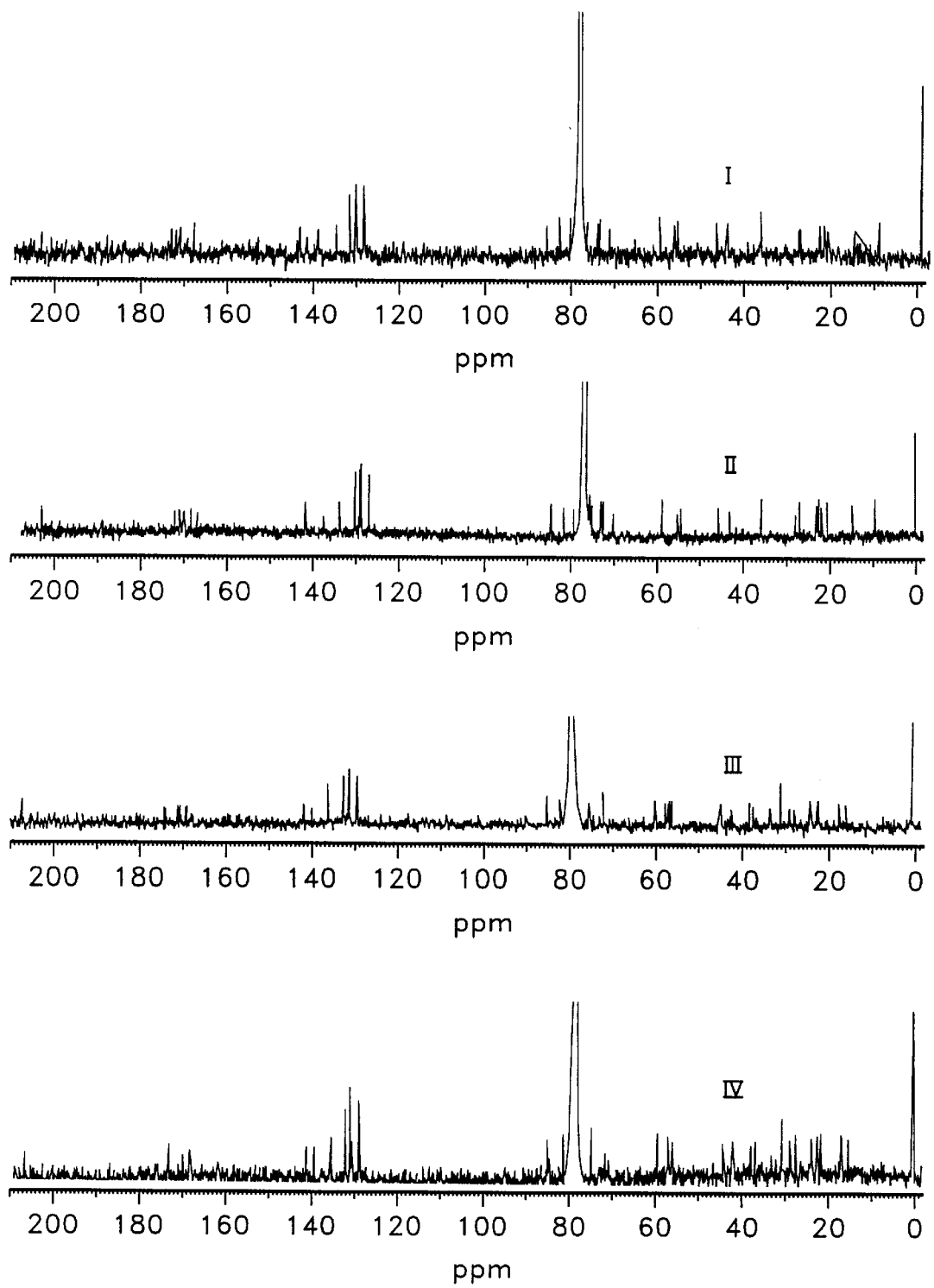
FIG. 11 is a comparison of $^{13}$C-NMR spectra of pure dibromocephalomannine (I and II) and pure dibromo-7-epi-cephalomannine diastereomers (III and IV).

FIG. 7–10 are respective $^1$H-NMR spectra of dibromocephalomannine and dibromo-7-epi-cephalomannine diastereomer, and FIG. 11 shows $^{13}$C-NMR spectra for these diastereomers. All of the spectra are summarized below.

DiBr-I $^1$H—NMR in $CDCL_3$
(300 MHz in ppm; side chain and some important protons only)

| Chemical Shift (ppm) | Assignments |
|---|---|
| 3.36 (bd, 4.9, 1H) | (HO—C—C=O)(HO-2'a) |
| 4.74 (bd, 4.9, 1H) | (H—C—C=O)(HO-2$_b$') |
| 5.68 (d, 1H)- | (N—CH—)(H-3') |
| 4.62 (qt, 6.6, 1H)- | (>CH—Br)(H-3") |

DIBr-I ¹H—NMR in CDCL₃
(300 MHz in ppm; side chain and some important protons only)

| Chemical Shift (ppm) | Assignments |
|---|---|
| 1.81 (d, 6.6, 3H)- | (Br—C—C$\underline{H}_3$)(3H-4") |
| 1.98 (s, 3H)- | (Br—C—C$\underline{H}_3$)(3H-5")<br>—C=O |
| 2.35 (s, 3H)- | (—O—C(=O)—C$\underline{H}_3$)(3H-4) |
| 2.68 (m, 1H)- | (—C$\underline{H}_2$—)(H-6a) |
| 1.78 (m, 1H)- | (—C$\underline{H}_2$—)(H-6B) |
| 4.41 (m, 1H)- | (-CH-)(H-7a) |
| 2.46 (d, 1H)- | (—C—)(H-7b)<br>OH |
| 6.28 (s, 1H)- | (—C$\underline{H}$—O—OCCH₃)(H-10) |
| 2.22 (m, 2H)- | (—C$\underline{H}_2$—)(2H-14,a,b) |
| 2.01 (s, 3H)- | (—C$\underline{H}_3$)(3H-C-1S) |
| 4.20 (d, 8.4H) | (—C$\underline{H}_2$—)(H-20a,) |
| 4.29 (d, 8.4, 1H) | (—C$\underline{H}_3$—)(H-20B) |

DIBr-I ¹³C—NMR
300 MHz in ppm; side chain and some important carbons only

| Chemical Shift (ppm) | Assignments |
|---|---|
| 172.3 | (C-1'; C=O) |
| 73.0 | (C-2') |
| 54.6 | (C-3') |
| 172.0 | (C-1"; C=O) |
| 58.8 | (C-2") |
| 55.4 | (C-3") |
| 22.7 | (C-4") |
| 27.6 | (C-5") |
| 203.5 | (C-9; C=O) |

DIBr-II ¹H—NMR in CDCL₃
(300 MHz in ppm; side chain and some important protons only)

| Chemical Shift (ppm) | Assignments |
|---|---|
| 3.42 (bs, 1H) | —(H$\underline{O}$—C—C=O)(HO-2'a) |
| 4.74 (d, 4.91H ) | —(—$\underline{H}$C—C=O)(H-2b) |
| 5.68 (d, 1H) | —(—N—C$\underline{H}$)(H-3') |
| 4.62 (qt, 6.6, 1H) | —(>C$\underline{H}$—Br)(H-3") |

DIBr-II ¹H—NMR in CDCL₃
(300 MHz in ppm; side chain and some important protons only)

| Chemical Shift (ppm) | Assignments |
|---|---|
| 1.81 (d, 6.6, 3H) | —(Br—C—C$\underline{H}_3$)(3H-4") |
| 1.98 (s, 3H) | —(Br—C—C$\underline{H}_3$)(3H-5")<br>—C=O |
| 2.35 (s, 3H) | —(O—C(=O)—C$\underline{H}_3$)(3H-4) |
| 2.68 (m, 1H) | —(—C$\underline{H}_2$—)(H-6a) |
| 1.78 (m, 1H) | —(—C$\underline{H}_2$—)(H-6B) |
| 4.41 (m, 1H) | —(—C$\underline{H}$)(H-7a)<br>OH |
| 2.48 (m, 1H) | —(—C$\underline{H}$)(H-7b) |
| 6.28 (s, 1H) | —(—C$\underline{H}$—O—COCH₃)(H-10) |
| 2.22 (m, 2H) | —(—C$\underline{H}_2$—)(2H-14a, b) |
| 2.01 (s, 3H) | —(—C$\underline{H}_3$)(3H-C-18) |
| 4.29 (d, 8.41H) | —(—C$\underline{H}$—)(2H-20a) |
| 4.20 (d, 8.4, 1H) | —(—C$\underline{H}_3$—)H-2aB |

DIBr-II ¹³C—NMR
(300 MHz in ppm; side chain and some important carbons only)

| Chemical Shift (ppm) | Assignments |
|---|---|
| 172.3 | (C-1'; C=O) |
| 72.9 | (C-2') |
| 54.6 | (C-3') |
| 171.2 | (C-1") C=O |
| 58.8 | (C-2") |
| 55.2 | (C-3") |
| 22.7 | (C-4") |
| 27.9 | (C-5") |
| 203.5 | (C-9; C=O) |

DIBr-III ¹H—NMR in CDCL₃
(300 MHz in ppm; side chain and some important protons only)

| Chemical Shift (ppm) | Assignments |
|---|---|
| 3.23 (d, 1H) | —(H$\underline{O}$—C—C=O)(HO 2'a) |
| 4.76 (d, 1H) | —(—$\underline{H}$C—C=O)(H-2b) |
| 5.65 (d, 1H) | —(—N—C$\underline{H}$)(H-3') |
| 4.62 (qt, 6.6, 1H) | —(>C$\underline{H}$—Br)(H-3") |

DIBr-III $^1$H—NMR in CDCL$_3$
(300 MHz in ppm; side chain and some important protons only)

| Chemical Shift (ppm) | Assignments |
|---|---|
| 1.28 (s, 3H) | —(Br—C(—CH$_3$)—)(3H-4″) |
| 1.28 (s, 3H) | —(Br—C(—CH$_3$)(—C=O)—)(3H-5″) |
| 1.72 (s, 3H) | —(O—C(=O)—CH$_3$)(3H-4) |
| 2.45 (t, 2H) | —(—CH$_2$—)(H-6a,b) |
| 3.72 (m, 1H) | —(—CH(—OH)—)(H-7a) |
| 4.62 (s, 1H) | —(—C(—OH)—)(H-7b) |
| 6.79 (s, 1H) | —(—CH—O—COCH$_3$)(H-10) |
| 2.05–2.42 (m, 2H) | —(—CH$_2$—)(2H-14a, b) |
| 2.18 (s, 3H) | —(—CH$_3$)(3H-C-18) |
| 4.38 (m, 1H) | —(—CH—)(H-20a) |
| 4.38 (m, H) | —(—CH$_3$—)1H-20B) |

DIBr-III $^{13}$C—NMR
(300 MHz in ppm; side chain and some important carbons only)

| Chemical Shift (ppm) | Assignments |
|---|---|
| 169.3 | (C-1′; C=O) |
| 72.9 | (C-2′) |
| 54.0 | (C-3′) |
| 172.5 | (C-1″) C=O |
| 57.7 | (C-2″) |
| 54.5 | (C-3″) |
| 22.6 | (C-4″) |
| 29.4 | (C-5″) |
| 207.1 | (C-9; C=O) |

DIBr-IV $^1$H—NMR in CDCL$_3$
(300 MHz in ppm; side chain and some important protons only)

| Chemical Shift (ppm) | Assignments |
|---|---|
| 3.23 (d, 1H) | —(HO—C(—C=O)—)(HO-2′a) |
| 4.76 (d, 1H) | —(—HC—C=O)(H-2b) |
| 5.65 (d, 1H) | —(—N—CH)(H-3′) |
| 4.62 (qt, 1H) | —(>CH—Br)(H-3″) |
| 1.28 (s, 3H) | —(Br—C(—CH$_3$)—)(3H-4″) |
| 1.98 (s, 3H) | —(Br—C(—CH$_3$)(—C=O)—)(3H-5″) |
| 1.72 (s, 3H) | —(O—C(=O)—CH$_3$)(3H-4) |
| 2.45 (t, 2H) | —(—CH$_2$—)(H-6a, b) |
| 3.72 (m, 1H) | —(—CH—)(H-7a) |
| 4.62 (s, 1H) | —(—C(—OH)—)(H-7b) |
| 6.79 (s, 1H) | —(—CH—O—COCH$_3$)(H-10) |
| 2.05–2.42 (m, 2H) | —(—CH$_2$—)(2H-14a, b) |
| 2.18 (s, 3H) | —(—CH$_3$)(3H-C-18) |
| 4.38 (m, 1H) | —(—CH—)(1H-20a, a) |
| 4.38 (m, 1H) | —(—CH$_3$)(1H-20B) |

DIBr-IV $^{13}$C—NMR
(300 MHz in ppm; side chain and some important carbons only)

| Chemical Shift (ppm) | Assignments |
|---|---|
| 172.5 | (C-1′; C=O) |
| 72.1 | (C-2′) |
| 54.1 | (C-3″) |
| 171.1 | (C-1′ ′; C=O) |
| 57.8 | (C-2″) |
| 54.3 | (C-3″) |
| 22.6 | (C-4″) |
| 29.4 | (C-5″) |
| 207.1 | (C-9; C=O) |

Physico-chemical properties of the dibromocephalomannine/dibromo-7-epi-cephalomannine diastereomers of this invention are summarized below in Table 4:

TABLE 4

Physico-Chemical Properties of Bromo-Analogues of Paclitaxel

| Property | DiBr-I | Di-Br-II | DiBr-III | DiBr-IV |
|---|---|---|---|---|
| Appearance | Off-white to slightly yellowish crystals | Off-white to slightly yellowish crystals | Off-white to slightly yellowish crystals | Off-white to slightly yellowish crystals |
| Melting point | 185–187° C. | 171–173° C. | 166–168° C. | 163–165° C. |
| Molecular formula | $C_{45}H_{53}O_{14}NBr_2$ | $C_{45}H_{53}O_{14}NBr_2$ | $C_{45}H_{53}O_{14}NBr_2$ | $C_{45}H_{53}O_{14}NBr_2$ |
| Molecular weight | 991.7 | 991.7 | 99.1.7 | 991.7 |
| $[\alpha]24.2_D$ | −41.3° | −44.4° | −45.40° | 44.1° C. |
| IR*(cm$^{-1}$) | 3500, 1105, 1070; 3420, 1670, 1580; 3110, 3060, 1605, 1505, 770, 710; 2960, 2915, 2870, 1465, 1370; 3020, 1670, 1310, 980; 1730, 1270; 1715, 1240; 1730, 1180; 855 | | | |
| UV $\lambda_{max}$; ($\epsilon$) | 226.0 nm; 14732 | 226.0 nm; 12415 | 219.4 nm; 37900 | 218.4 nm; 20013 |
| TLC** ($R_f$) solvent systems: A | 0.34 | 0.37 | 0.63 | 0.65 |
| :B | 0.28 | 0.30 | 0.54 | 0.57 |
| HPLC*** (RT) | | | | |
| condition 1: | 43.81 min. | 45.01 min. | 69.68 min. | 71.92 min. |
| condition 2: | 46.65 min. | 48.39 min. | 69.66 min. | 72.60 min. |

*The IR spectra of DiBr-I–IV are superimposable.
**Solvent System A: Methanol-1,2,-Dichloroethane, either (1:9), or (1:10)
Solvent System B: Hexane-Chloroform-Ethyl Acetate-Methanol-(2:6:1.5:0.5)
***Condition 1: <u>Column</u>: ES Industries FSP (Pentafluorophenyl) 4.6 mm ID × 250 mm, 5 um particle size, 60Å pore size; <u>mobile phase</u> - water - acetonitrile - methanol - (41:39:20); <u>flow rate</u> 0.50 ml/min; <u>separation mode</u> - isocratic; <u>detector</u> - Waters 990 Photodiode Array Detector; elution monitored at 227 nm; <u>injection volume</u> - 20 ul.
Condition 2: Column: Phenomenex 4.6 mm ID × 250 mm, 5 um particle size, 80Å pore size; <u>mobile phase</u> - water - acetonitrile - methanol - (45:40:15); <u>flow rate</u> - 0.50 ml/min; <u>separation mode</u> - isocratic; <u>detector</u> - Waters 490 programmable multiwavelength detector, elution monitored at 227 nm; <u>injection volume</u> - 80 ul total mixture.

EXAMPLE IV

In Vitro and In Vivo studies showing Antitumor Efficacy of a Mixture of Dibromocephalomannine/Dibromo-7-epi-cephalomannine Diastereomers Which Correlate to Known Paclitaxel Antitumor Efficacy.

As is known, paclitaxel, for example Taxol® (Bristol-Myers Squibb) and its derivative Taxotere® (Rhône-Poulenc) exhibit highly desirable antitumor efficacy against a number of tumors. These antineoplastic drugs act in a unique manner by preventing depolymerization of tubulin forming microtubules of the mitotic spindle which is essential for cell division, and thus cause cell division to cease along with tumor cell proliferation. The mechanism of action of paclitaxel, its pharmacology, etc. is described, for example, in Rowinsky et al. Taxol: A Novel Investigational Antimicrotuble Agent, J. Natl. Cancer Inst., 82:1247 (1990).

In accordance with this invention, the mixture of novel dibromocephalomannine/dibromo-7-epi-cephalomannine diastereomers has been found to exhibit strong paclitaxel-like antitumor efficacy in vitro and in vivo, thereby providing a valuable addition to the arsenal of antitumor therapeutic agents and an important alternative to paclitaxel and its known derivatives, such as Taxotere.

1. In Vitro Studies (NCI)

The following in vitro studies were conducted by the National Cancer Institute's Developmental Therapeutics Program, and demonstrate the strong antitumor efficacy of the inventive dibromocephalomannine diastereomers comparable to that of paclitaxel.

Figure 12C:
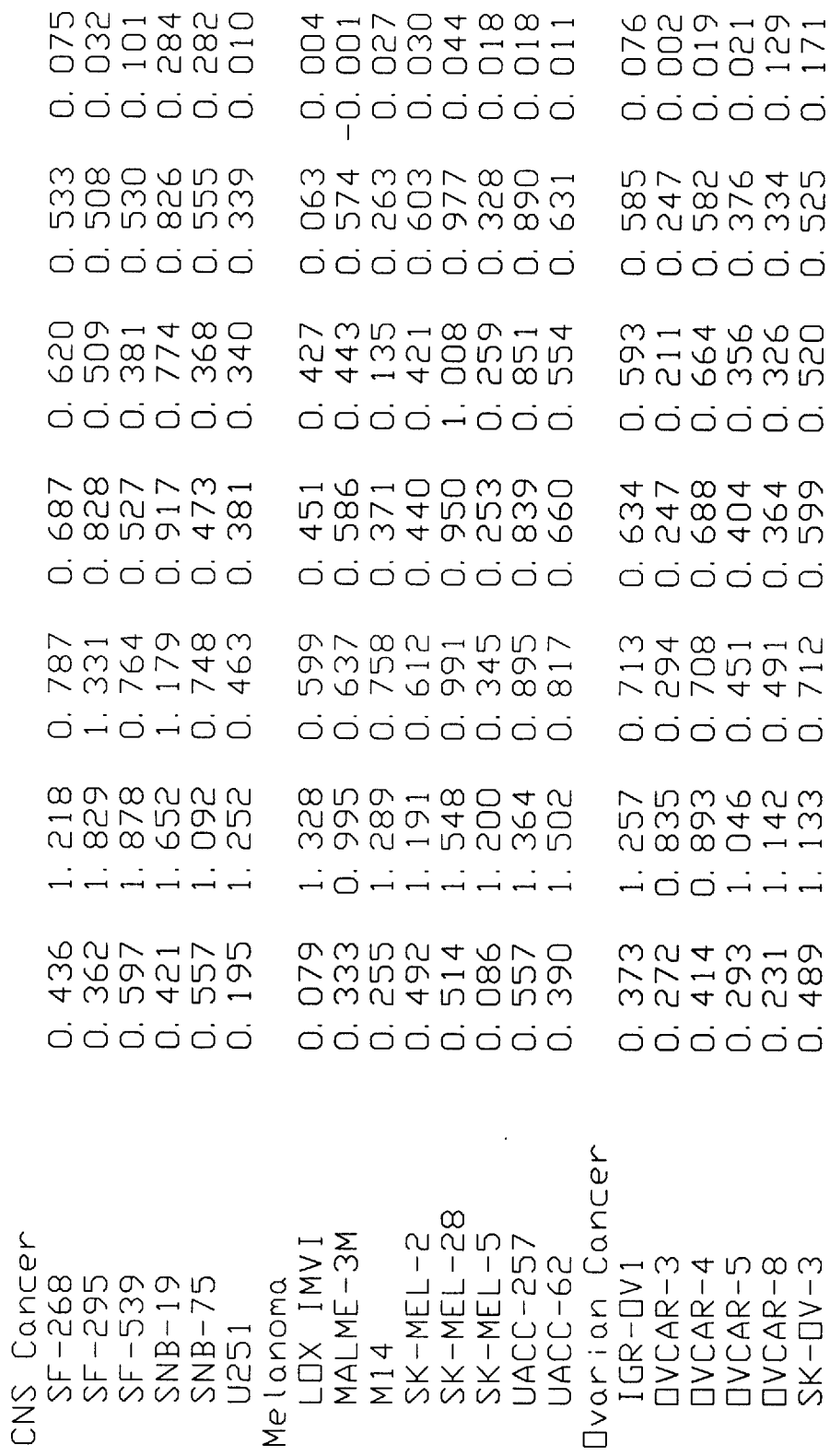
FIG. 12 is a data sheet of in vitro testing results of a mixture of dibromocephalomannine diastereomers I and II in a screen of sixty human tumor cell lines.
Figure 13B:
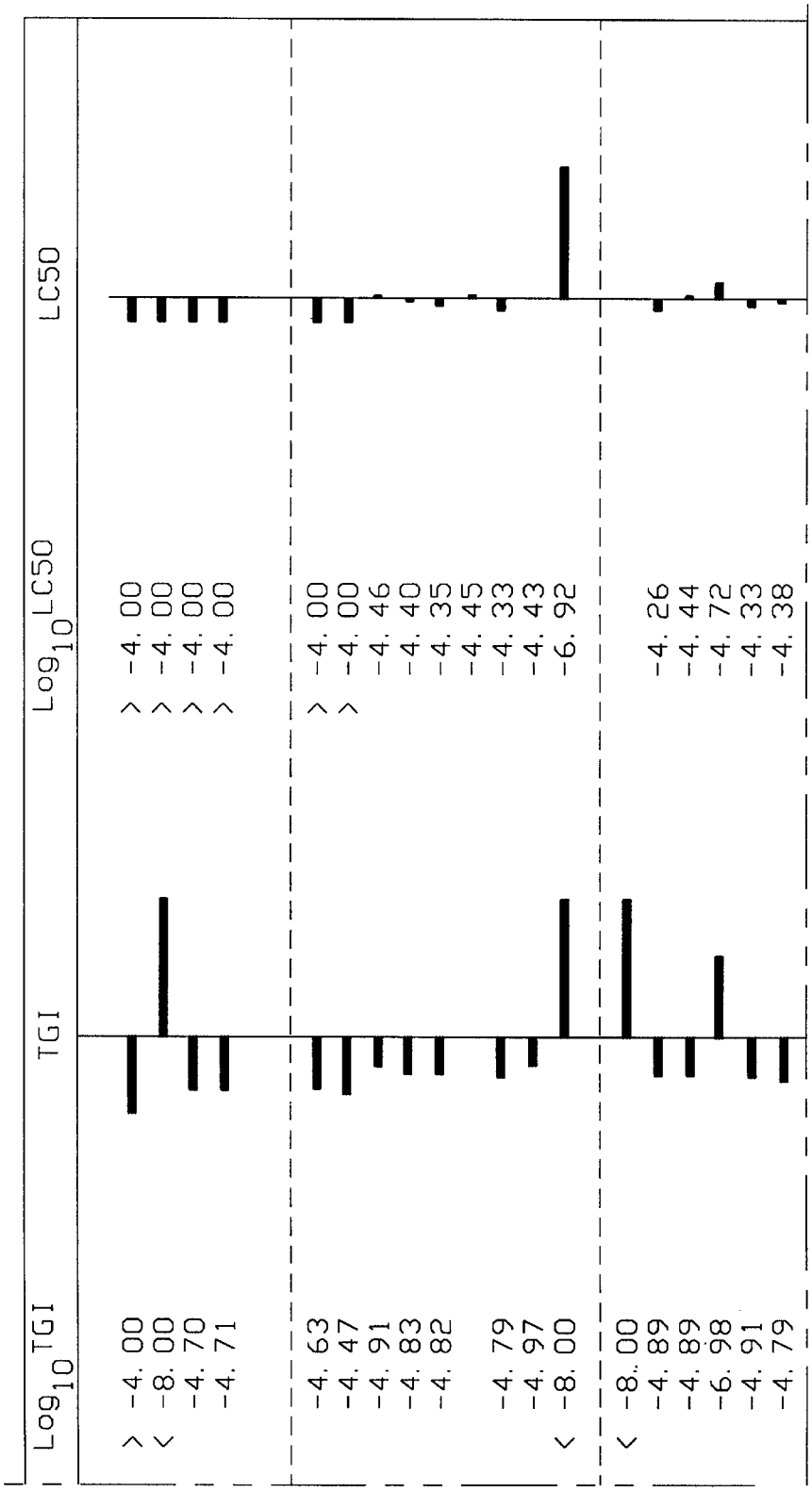
FIG. 13 are mean graphs of dose response of a mixture of dibromo-cephalomannine diastereomers I and II in a screen of sixty human tumor cell lines.
Figure 13C:
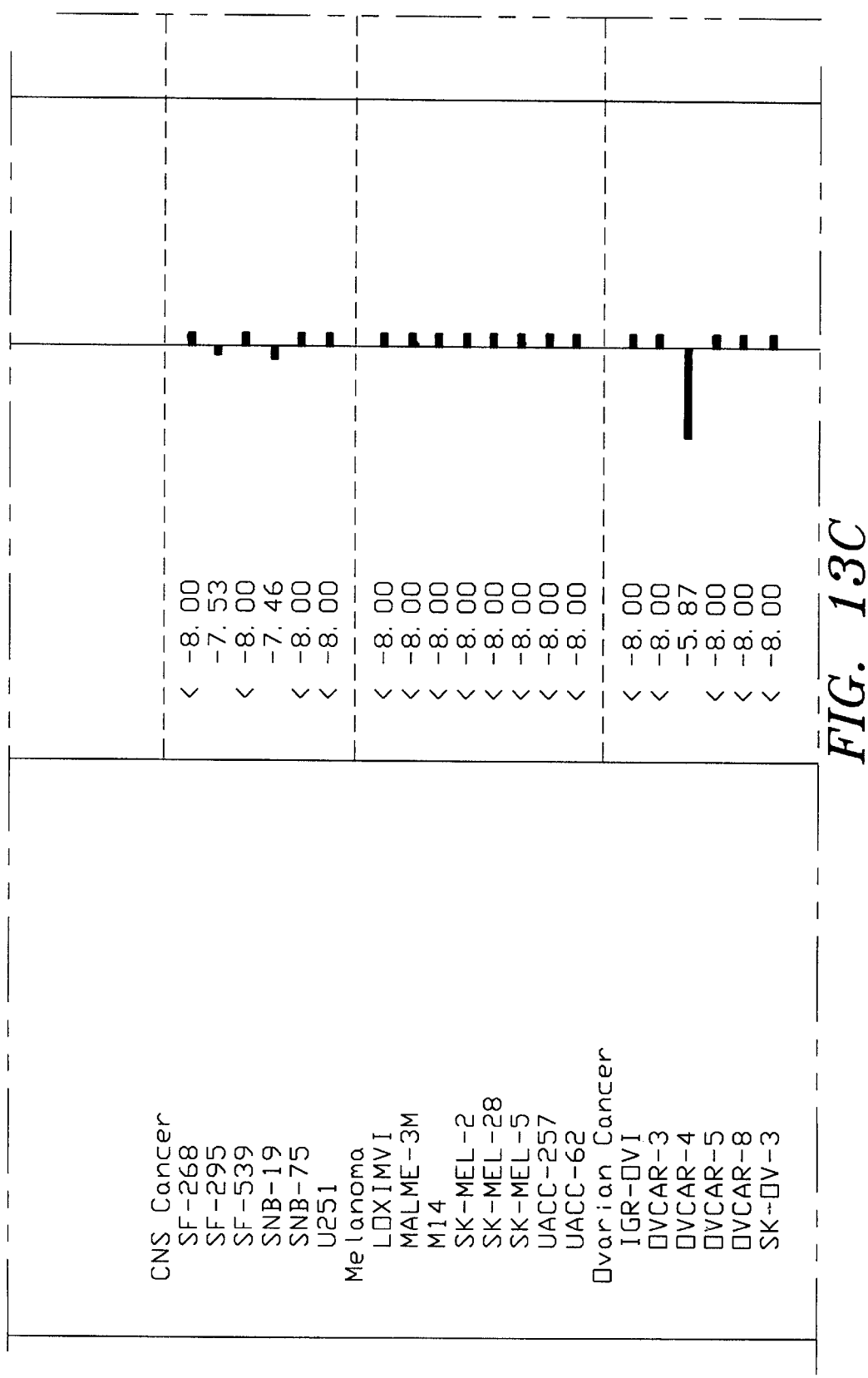
Figure 13D:
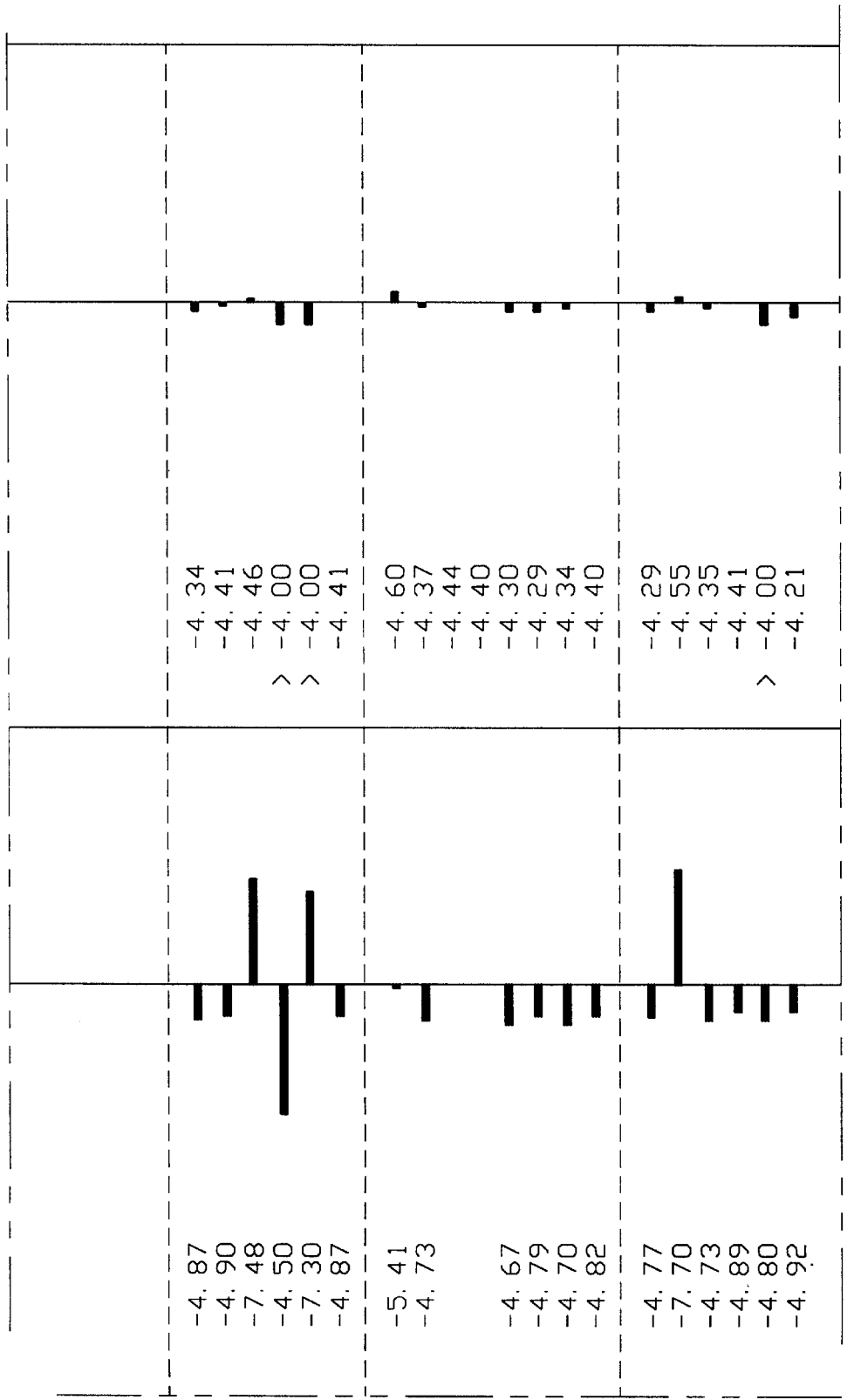
Figure 13E:
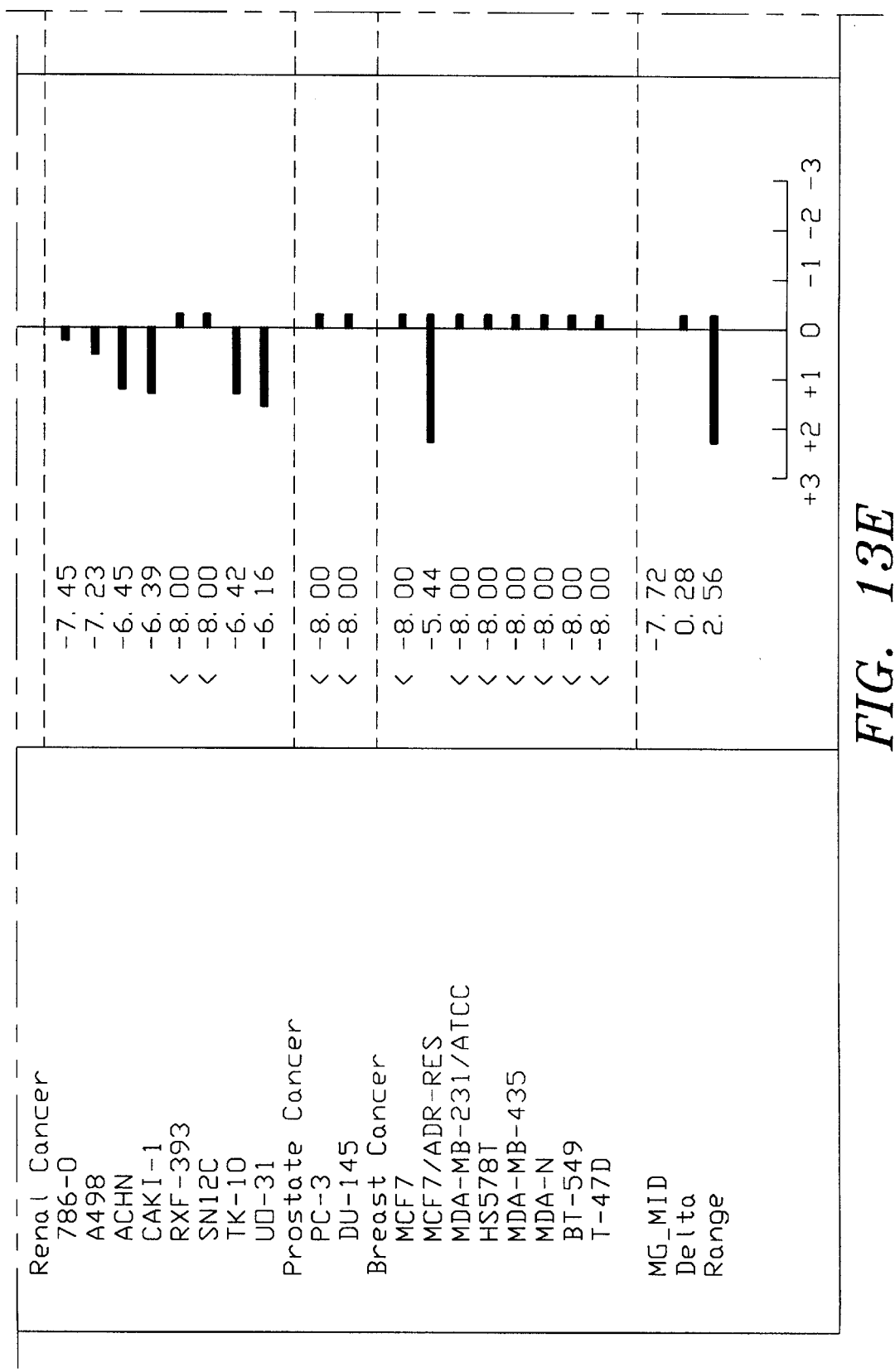
Figure 13F:
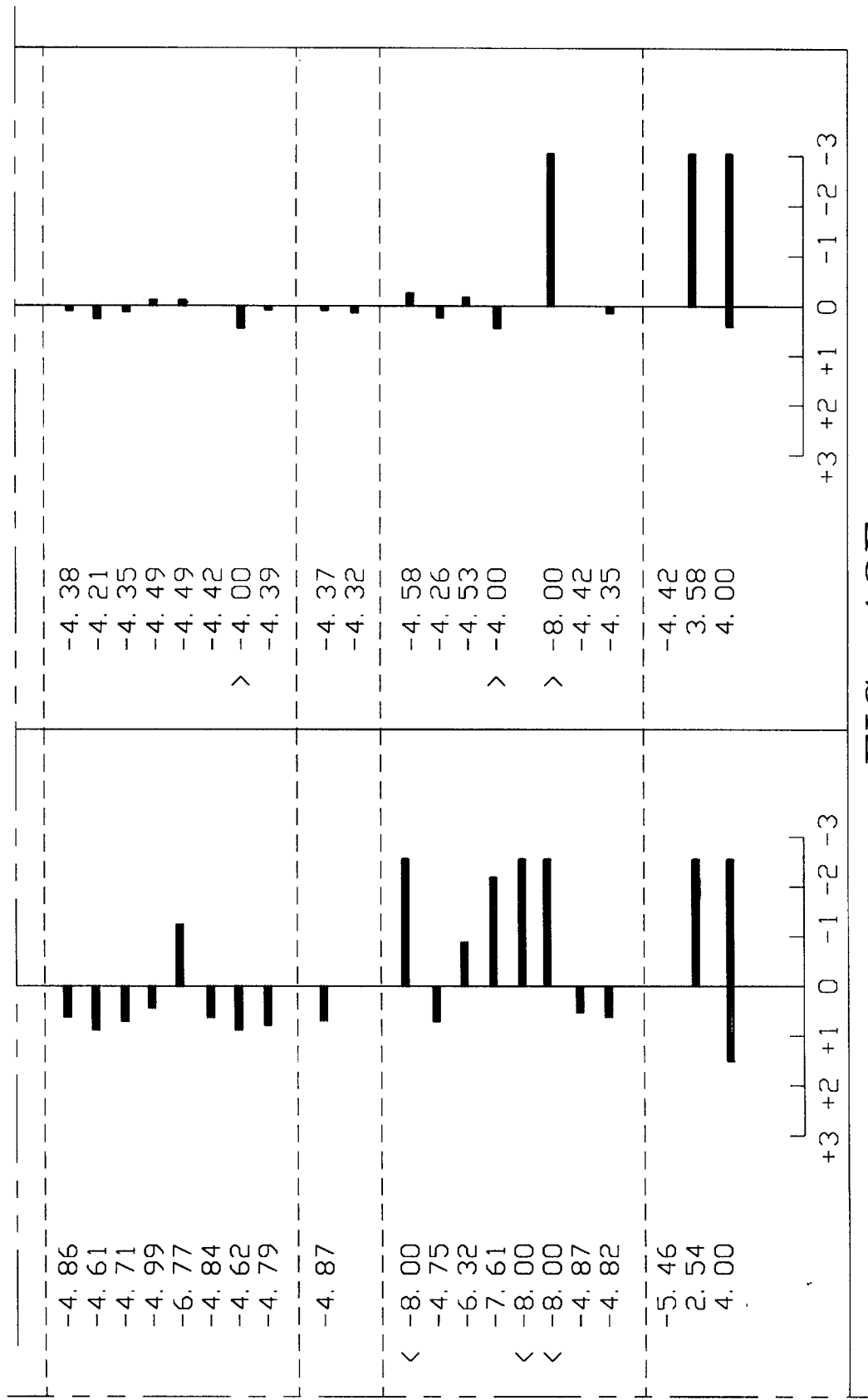
Figure 14A:
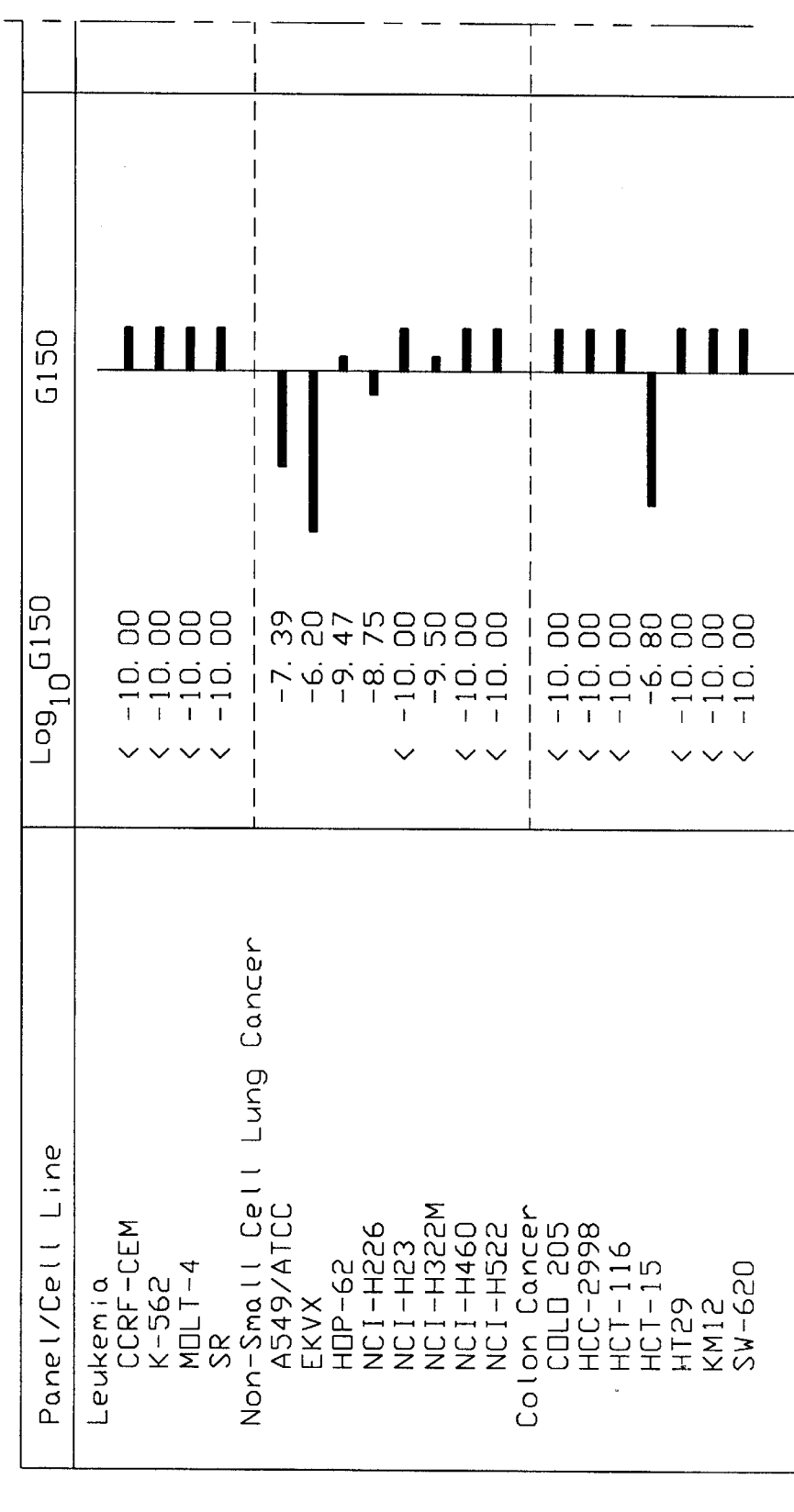
FIG. 14 are mean graphs of dose response of paclitaxel in a screen of sixty human tumor cell lines.
Figure 14B:
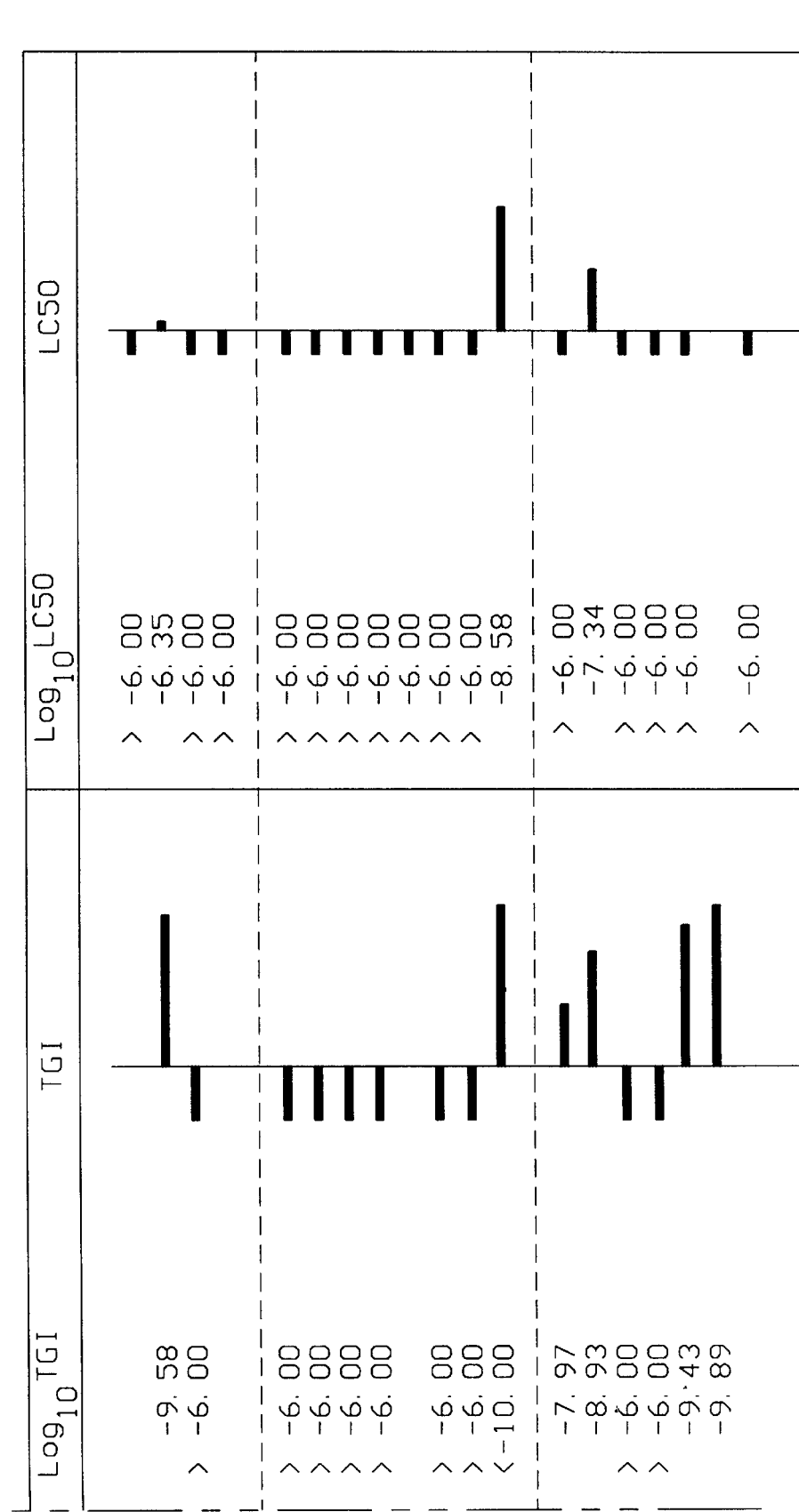
Figure 14C:
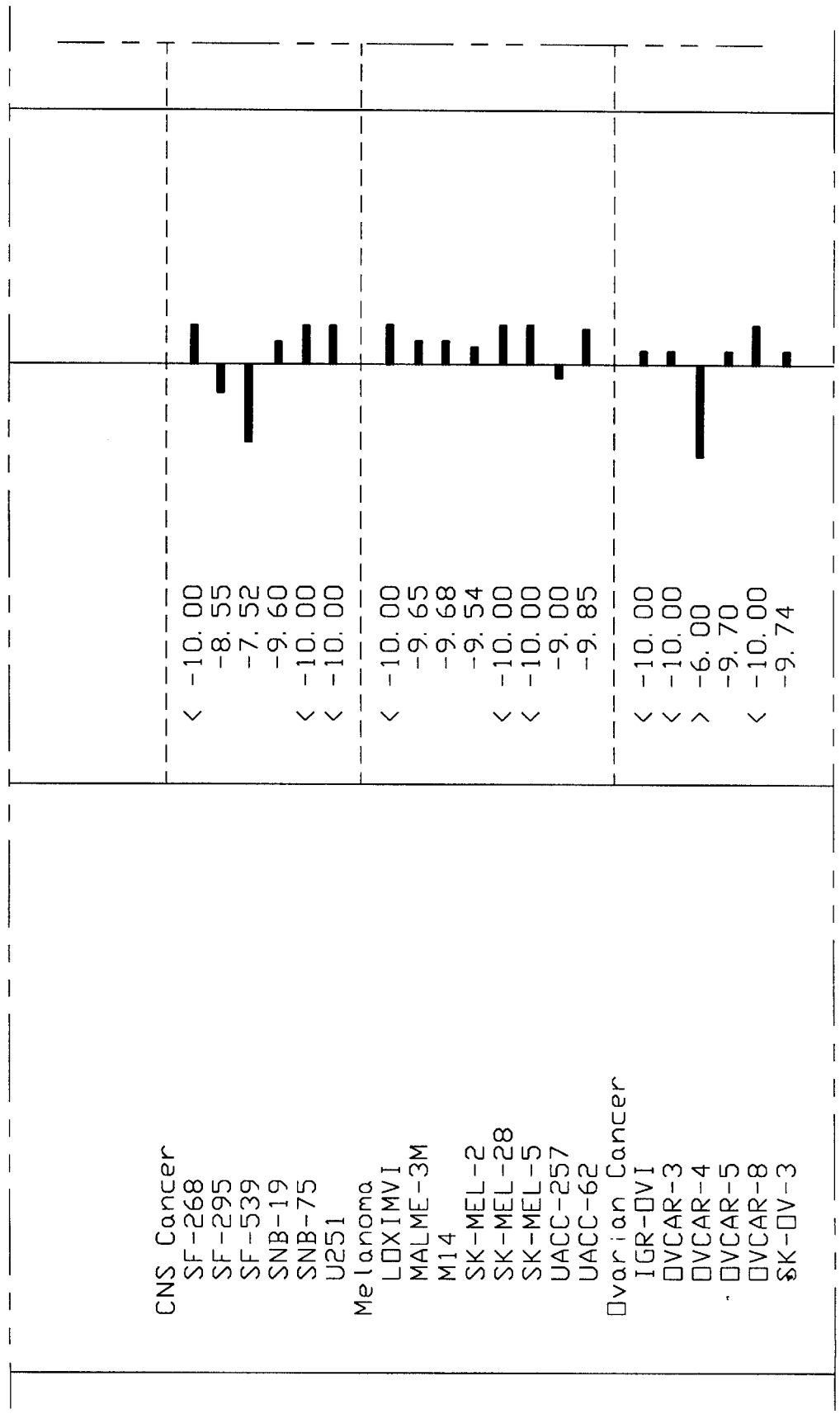
Figure 14D:
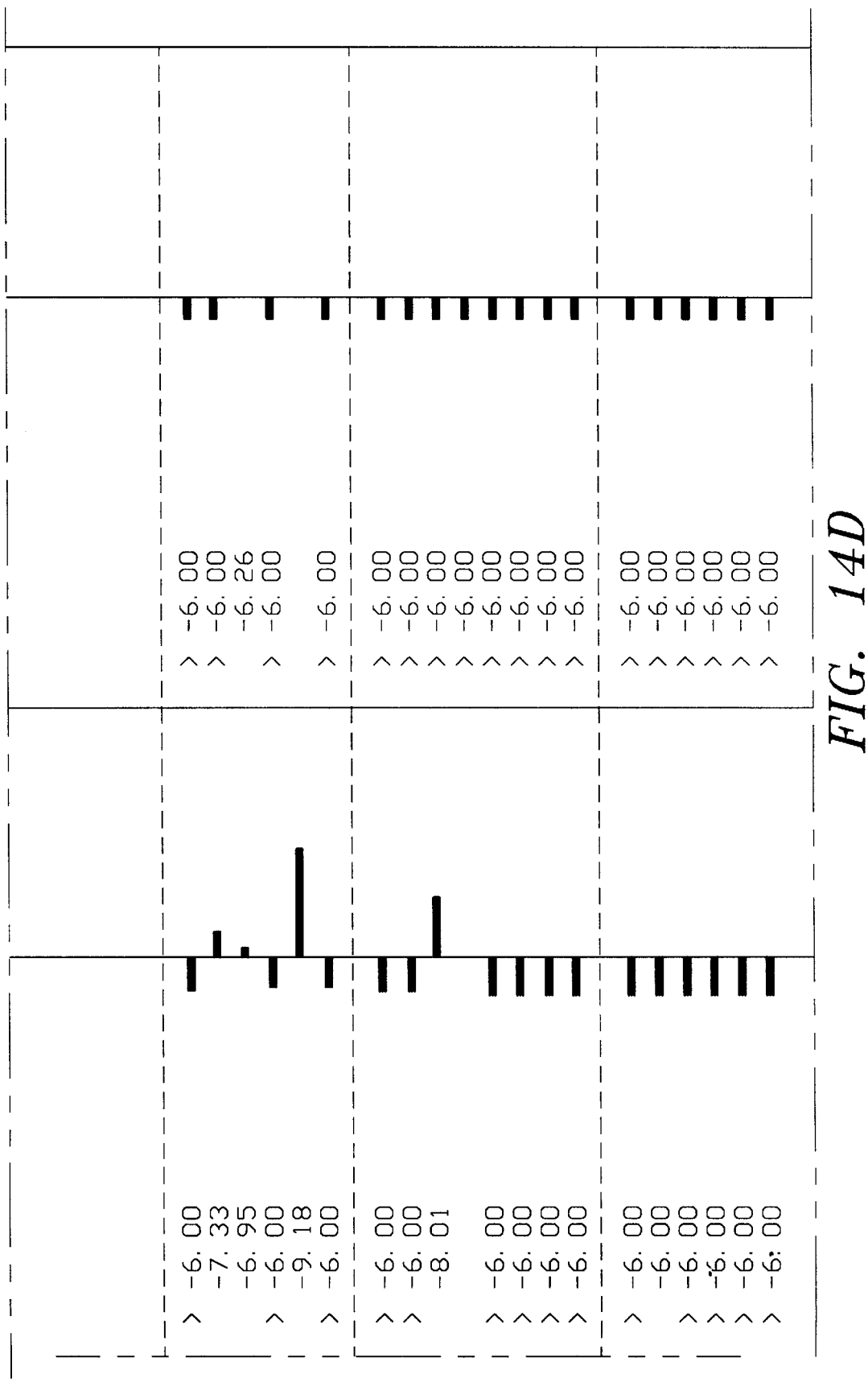
Figure 14E:
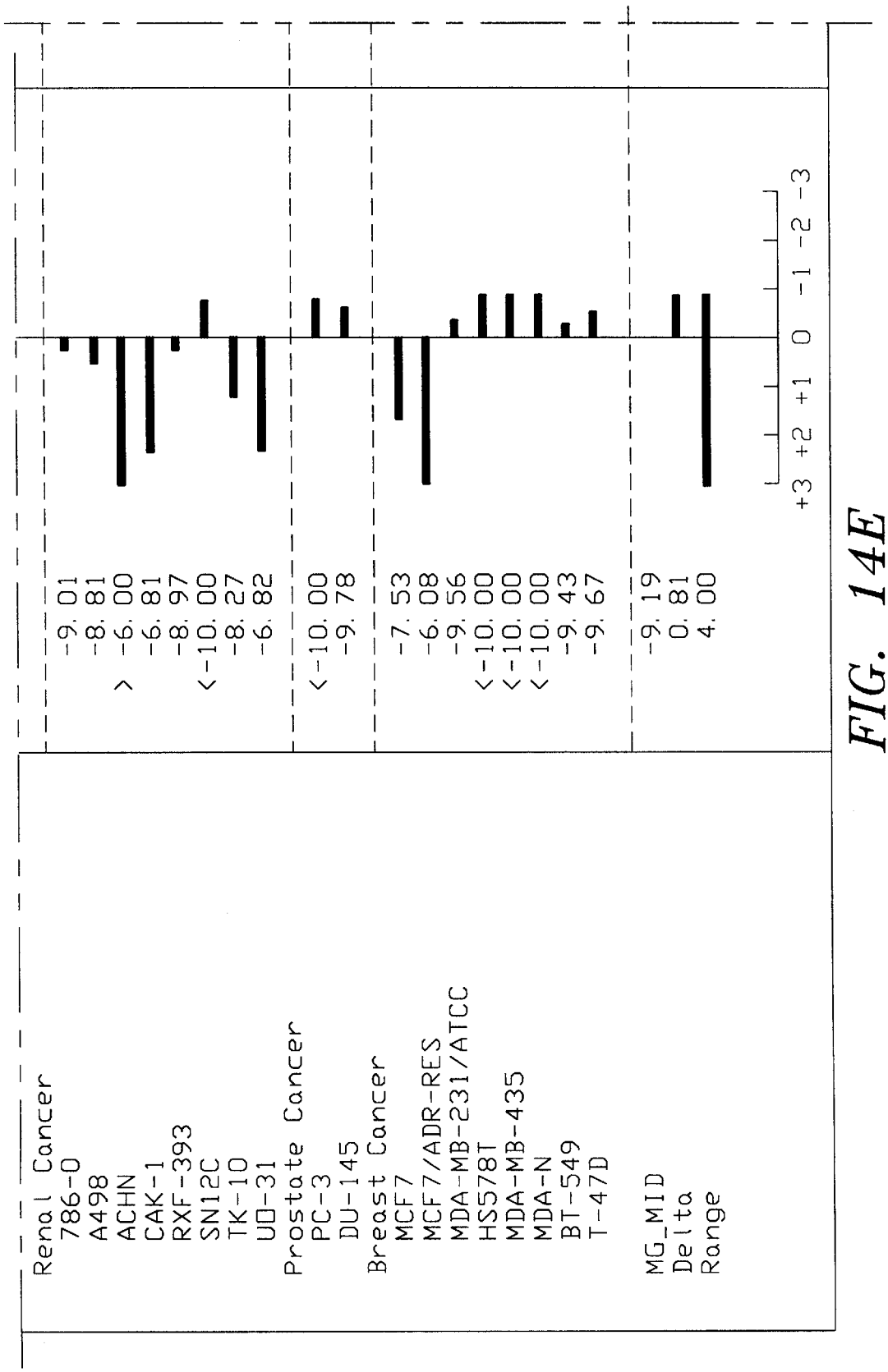
Figure 14F:
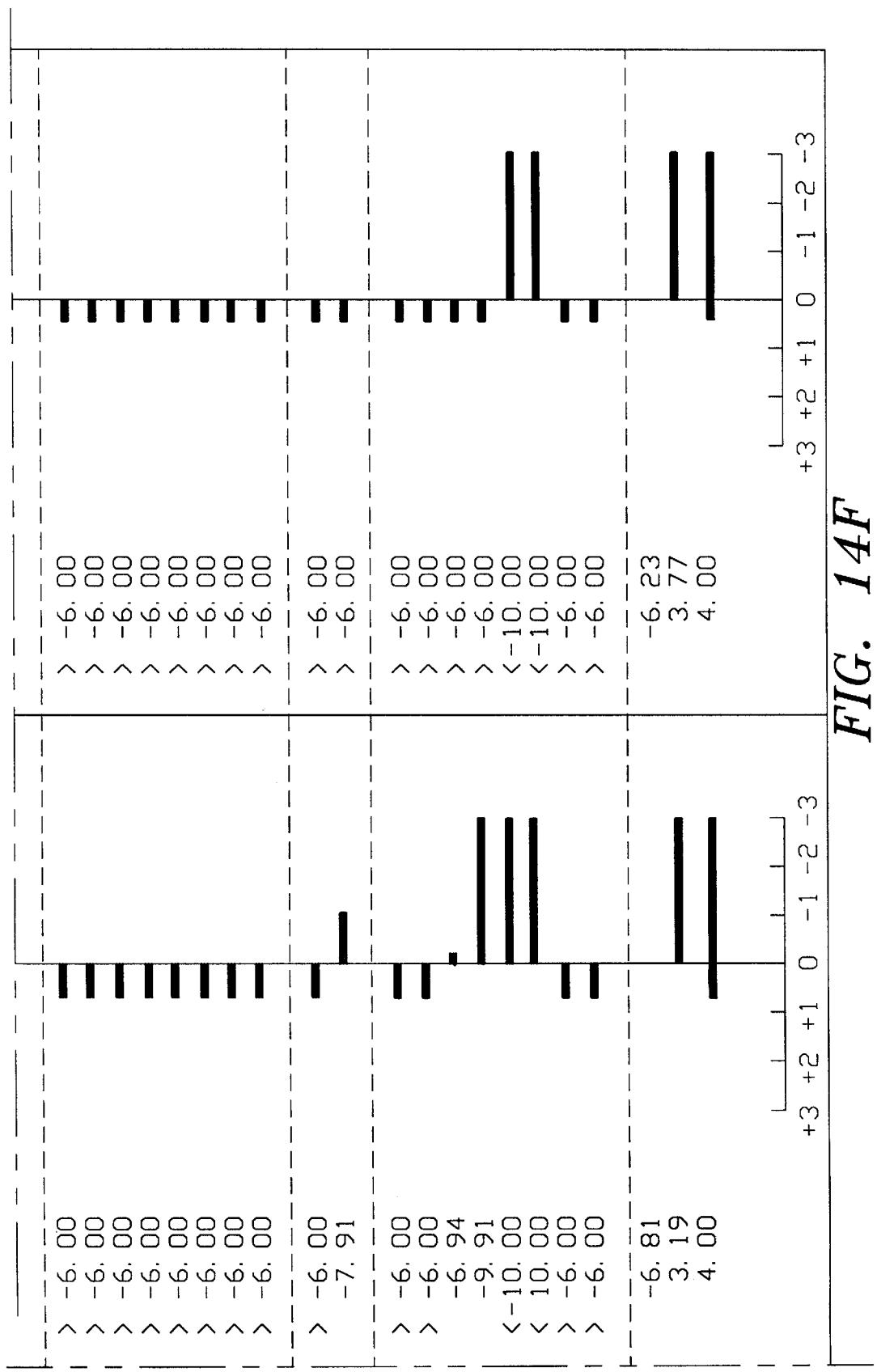

The Developmental Therapeutics Program provides as a service to the public an in vitro anticancer drug discovery screen using a panel of sixty different human tumor cell lines over which candidate drugs are tested at defined ranges of concentrations. See Boyd et al., Drug Development Research 34:91–109 (1995), the entirety of which is incorporated herein by reference. As discussed in Boyd et al., the screen is designed and operated in such a manner that both relative and absolute sensitivities of each of the cell lines comprising the screen are reproducible to the degree that a characteristic profile ("fingerprint") of a respective cell lines' response to a drug candidate can be generated. Recent studies of the in vivo counterpart of the NCI in vitro screen have indicated the in vitro screen to be an effective selector of compounds with in vivo anticancer efficacy. See Grever et al., Proc. Am. Assoc. Cancer Res. 35:369 (1994). Operation and interpretation of the screen are discussed in detail in Boyd et al., as well as in several other articles cited therein and thus need not be repeated here, except comparative results obtained from the screen between the mixture of the novel 2"3"-dibromocephalomannine and dibromo-7-epi-cephalomannine diastereomers represented as compound "XCLY-401759 analog" and that of the known antitumor compound, paclitaxel. In vitro antitumor efficacy of XCLY- 401759 is shown in FIGS. 12 and 13, Testing Results and Mean Graphs, respectively.

In corresponding manner, in vitro antitumor efficacy is shown in FIG. 14 by dose response represented by a mean graph of paclitaxel.

Discussion of Results

In the NCI in vitro anticancer drug screen the effect of an antitumor candidate, i.e. XCLY-401759 of the present invention, on a cell line, percentage growth (PG) and calculated response parameters, are discussed in detail in Boyd et al., Data display and analysis strategies for the NCI—disease-oriented in vitro antitumor drug Screen, Cytotoxic Anticancer Drugs: Models and Concepts for Drug Discovery and Development, Kluwer Academic Publishers, Amsterdam, pp. 11–34 (1992), and Monks et al. Feasibility of a high-flux anticancer drug screen utilizing a diverse panel of human tumor cell lines in culture, J. Natl. Cancer Inst. 83:757–766 (1991), the entire disclosures of which are incorporated herein by reference. In general, in the screening data report, FIG. 9, and mean graphs, FIGS. 10 and 11, "$GI_{50}$" represents the 50% growth inhibition factor, "TGI" represents a total growth inhibition, or cytostatic level of effect, and "$LC_{50}$" represents a lethal concentration, or net cell killing or cytotoxicity parameter. Values accompanied by a "<" signify that the dosage level or real value is a value that is something less than the lowest tested concentration, and values accompanied by a ">" sign indicate that the effective dosage or real value is a level greater than the highest tested concentration.

The mean graphs are obtained from $GI_{50}$, TGI and $LC_{50}$ concentrations obtained for compounds tested against each cell line in the NCI in vitro screen. A detailed discussion of mean graph construction is provided in Boyd et al. (1995). In interpreting the mean graphs in general, a bar projecting to the right represents sensitivity of a particular cell line to an anticancer candidate in excess of the average sensitivity of all tested cell lines, while bars extending to the left represent cell lines which are less sensitive on average to the anticancer candidate. As the bar scales are logarithmic, a bar which extends, for example, 2 or 3 units to the right of the vertical reference line in, say a $GI_{50}$ mean graph, indicates that the anticancer candidate achieved a response parameter for a particular cell line at a concentration one-hundredth to one-thousandth of the mean concentration required over all cell lines, therefore indicating that the particular tumor cell line is unusually sensitive to the tested candidate.

Turning now to FIG. 13, the candidate XCLY-401759 of this invention shows a relatively high magnitude of effect in TGI, for example, on Leukemia cell line HL-60(TB); Non-Small Cell Lung Cancer line NCI-H522; Colon Cancer cell lines COLO 205 and HT 29; CNS Cancer cell lines SF-539 and SNB-75; Ovarian Cancer Cell line OVCAR-3; Renal Cancer cell line RXF-393; and Breast Cancer cell lines MCF7, MDA-MB-231/ATCC, HS 578T, MDA-MB-435 and MDA-N.

In comparison with FIG. 14, analysis of the well known antitumor compound paclitaxel, the XCLY-401759 candidate demonstrates an unusually high magnitude of response such as that of paclitaxel to Non-Small Cell Lung Cancer cell line NCI-H522 (<−8 v. <−10 for XCLY-401759 and paclitaxel, respectively). Compare also the respectively high magnitude of response of both XCLY-401759 and paclitaxel on Colon Cancer Cell line COLO 205 (<−8 v. −7.97); on CNS cancer cell line SNB-75 (−7.30 v. −9.18), and, for example, on Breast Cancer Cell line HS 5787 (−7.61 v. −9.91).

The high magnitude of effect of XCLY-401759 on many cell lines is perhaps more pronounced in $GI_{50}$ in which XCLY-401759 demonstrates a high response level in many of the same cell lines as does paclitaxel, such as, for example, with various tested colon cancer cell lines, melanoma cell lines, ovarian cancer cell lines, and renal cancer cell lines, and falls within the footprint of paclitaxel-like antitumor activity thereby reproducibly demonstrating the high antitumor efficacy of the novel XCLY-401759 mixture.

The strong paclitaxel-like antitumor efficacy of XCLY-401759 is further shown in correlation data generated by the NCI, as summarized below in Table 5. See Paull et al., J. NCI, 81:1088–1092 (1989).

TABLE 5

| | * NSC | LCONC | (MAX X) | CORR. COEFF. | (N) | CHEM-NAME |
|---|---|---|---|---|---|---|
| | | | NCI | | | |
| | COMPARE-CORR-G150 XCLY-401759, LCONC = −4.00M(BV) | | | | | |
| 1) | 125973 | −4.60 | 21 | 0.825 | 60 | PACLITAXEL |
| 2) | 999991 | 0.00 | 1 | 0.811 | 10 | MDR RHOD30 |
| 3) | 49842 | −5.60 | 127 | 0.755 | 60 | VINBLASTINE SULFATE |
| 4) | 3053 | −6.60 | 71 | 0.713 | 60 | ACTINOMYCIN D |
| 5) | 328426 | −5.60 | 19 | 0.699 | 60 | PHYLLANTHOSIDE |
| 6) | 337766 | −3.60 | 10 | 0.686 | 60 | BISANTRENE HCL |
| 7) | 330500 | −3.30 | 12 | 0.663 | 59 | MACBECIN II |
| 8) | 165563 | −3.70 | 14 | 0.618 | 60 | BRUCEANTIN |
| 9) | 58514 | −4.00 | 8 | 0.604 | 60 | CHROMOMYCIN A3 |
| 10) | 267469 | −3.70 | 13 | 0.590 | 60 | DEOXYDOXORUBICIN |
| 11) | 83265 | −3.90 | 15 | 0.586 | 60 | S-TRITYL-L-CYSTEINE |
| | | | NCI | | | |
| | | COMPARE-CORR-TGI | | | | |
| | | XCLY-401759, LCONC = −4.00M(BV) | | | | |
| 1) | 125973 | −4.60 | 20 | 0.830 | 59 | PACLITAXEL |
| 2) | 49842 | −5.60 | 128 | 0.727 | 59 | VINBLASTINE SULFATE |
| 3) | 332598 | −9.00 | 9 | 0.605 | 59 | RHIZOXIN |
| 4) | 153858 | −4.00 | 15 | 0.598 | 59 | MAYTANSINE |
| 5) | 67574 | −3.00 | 62 | 0.527 | 59 | VINCRISTINE SULFATE |
| 6) | 330500 | −3.30 | 12 | 0.501 | 59 | MACBECIN II |

TABLE 5-continued

| | NSC | LCONC | (MAX X) | CORR. COEFF. | (N) | CHEM-NAME |
|---|---|---|---|---|---|---|
| 7) | 328426 | −5.60 | 19 | 0.493 | 59 | PHYLLANTHOSIDE |
| 8) | 83265 | −3.90 | 15 | 0.484 | 59 | S-TRITYL-L-CYSTEINE |
| 9) | 325014 | −3.65 | 11 | 0.451 | 59 | BACTOBOLIN |
| 10) | 79037 | −3.30 | 58 | 0.430 | 59 | CCNU |
| 11) | 349156 | −3.65 | 11 | 0.422 | 59 | PANCRATIASTATIN |

*NSC-Test number
LCONC-Log of highest concentration tested
MAXX-Number of tests
COEFF.-Correlation Coeff.
CORR.-
(N)-Number of cell lines tested

2. IN VITRO STUDIES (SOUTHERN RESEARCH INSTITUTE)

In separate in vitro studies performed by an independent research group, Southern Research Institute, Birmingham, Ala. of the biological anti-cellular activity of XCLY-401759 on four human tumor lines, MX-1 (breast carcinoma), RXF-393 (renal cell carcinoma), NCI-H522 (lung adenocarcinoma) and OVCAR-3 (ovarian carcinoma), the XCLY-401759 compound was shown to yield a range of activity comparable to paclitaxel.

This testing was conducted using the aforesaid human tumor cell lines employing standard tissue culture techniques with semi-automated dye conversion assays. Selection of the human cell lines for testing was based at least in part on the following criteria: (1) histogenesis of clinical import, (2) adequate growth characteristics, and (3) experience with particular cell lines. The materials, methods and results of this study follow.

MATERIALS AND METHODS

Cell culture.

The human cell lines were propagated under sterile conditions in RPMI 1640 (Hyclone) with 10% fetal bovine serum (Sigma Chemical), 2 mM L-glutamine, and sodium bicarbonate (complete medium) and incubated at 37° C. in HEPA-filtered Sterilcult $CO_2$ tissue culture incubators (Forma) with 5% $CO_2$ and 95% humidity. The cell lines were subcultured weekly to bi-weekly and used in experiments. All lines were screened for mycoplasma contamination using GeneProbe™ (Fischer) and positive cultures were cured of contaminants over three passages using constant treatment with BM-Cyclin™ antibiotic combination (Boehringer Mannheim). Only lines confirmed as mycoplasma free were used in testing compounds for anticellular activity.

Anticellular activity experimental design.

For all experiments, cells were harvested and pelleted to remove the medium and then suspended in fresh complete medium. Samples were taken to determine cell density. The cell count was determined with a Coulter Model $Z_1$ cell counter and viability was measured with propidium iodide staining followed by analysis on a Coulter EPICS Elite Flow cytometer. The cell samples were adjusted with complete medium to a density of $5\times10^3$ cells/ml. Tissue culture cluster plates (96 well, cat No. 3595 Costar) were seeded with 100 ul cells ($5\times10^3$) and incubated as described.

On the day of treatment XCLY-401759 was dissolved in 100% ethanol then serially diluted in medium. The 0 dose control was mock-treated with medium. The appropriate wells (columns of 8) were treated with 5 concentration levels ($10^{-4}$, $10^{-5}$, $10^{-6}$, $10^{-7}$, and $10^{-8}$M). The highest dose of initial vehicle (ethanol in media) was ≦0.2% ethanol. A vehicle control was prepared at 0.2% to determine the effects of vehicle on the cell lines. Paclitaxel supplied by Xechem was dissolved in DMSO, serially diluted in medium and then added to the wells to achieve doses of $1\times10^{-8}$ and $1\times10^{-9}$M. Each cluster plate contained a cell control (8 wells, mock-treated with complete medium), a medium control (7 wells with medium used to substract out signal generated by medium conditions) and an air blank (1 well, for calibrating the plate reader). Once dosing was completed, the plates were stacked and wrapped in plastic film to reduce evaporation and incubated as described. Replicate sets of cluster plates had either 1 hour or 72 hour drug exposure. For the appropriate drug exposure, the plates were aseptically blotted on sterile towels and gently washed three times with medium. The samples were then fed with fresh medium, and the plates were wrapped in plastic wrap. The plates of both exposure sets were incubated to Day 7 and then processed to analyze for anticellular activity using the sulforhodamine B (SRB) procedure.

Results

In the 1 hour exposure XCLY-401759 concentration dependent activity was demonstrated in all the cell lines. The OVCAR-3 ovarian and NCI-H522 lung cell lines were the most sensitive to XCLY-401759. Paclitaxel activity was minimal at the two concentrations tested for MX-1, RXF 393 and OVACAR-3 tumor cell lines but NCI-H522 was sensitive to paclitaxel. The cell lines demonstrated increased sensitivity to both XCLY-401759 or paclitaxel when the exposure time was increased to 72 hours. MX-1 was relatively less sensitive than the other lines to the paclitaxel as well as XCLY-401759.

As shown, XCLY-401759 yielded a range of anticellular activity comparable to paclitaxel in four human tumor cell lines of various neoplastic disease originans.

The results are summarized below in Tables 6 and 7.

TABLE 6

SOUTHERN RESEARCH INSTITUTE
TREATMENT DAY 1 POST PLATING - PLATES WASHED 1 HR
AFTER $R_x$; PLATES ON DAY 7

| AGENT | TREAT-MENT (M) | % INHIBITION CELL LINE (CELLS PLATED 5.0E + 03 CELLS/WELL) | | | |
|---|---|---|---|---|---|
| | | RXF 393 | MX-1 | OVCAR-3 | NCI-H522 |
| XCLY-401759 | 1.0E-08 | 2.5 | 3.2 | 23.1 | 7.9 |
| | 1.0E-07 | 16.0 | 3.7 | 81.2 | 24.8 |
| | 1.0E-06 | 23.8 | 0.0 | 97.2 | 95.2 |
| | 1.0E-05 | 42.9 | 1.7 | 98.1 | 99.4 |
| | 1.0E-04 | 38.1 | 42.7 | 98.3 | 99.5 |
| VEHICLE CONTROL | | 0.0 | 0.8 | 7.0 | 4.5 |
| PACLITAXEL | 1.0E-09 | 3.7 | 1.6 | 1.2 | 8.3 |
| | 1.0E-08 | 13.8 | 4.0 | 7.1 | 35.1 |

TABLE 7

SOUTHERN RESEARCH INSTITUTE
TREATMENT DAY 1 POST PLATING - PLATES WASHED 72 HR
AFTER $R_x$; PLATES ON DAY 7

| AGENT | TREAT-MENT (M) | % INHIBITION CELL LINE (CELLS PLATED 5.0E + 03 CELLS/WELL) | | | |
|---|---|---|---|---|---|
| | | RXF 393 | MX-1 | OVCAR-3 | NCI-H522 |
| XCLY-401759 | 1.0E-08 | 64.8 | 29.4 | 98.7 | 97.2 |
| | 1.0E-07 | 80.7 | 45.4 | 99.1 | 98.6 |
| | 1.0E-06 | 85.1 | 76.5 | 99.2 | 98.4 |
| | 1.0E-05 | 81.6 | 75.4 | 98.8 | 98.3 |
| | 1.0E-04 | 100.0 | 98.3 | 100.0 | 100.0 |
| VEHICLE CONTROL | | 4.4 | 2.3 | 0.0 | 0.0 |
| PACLITAXEL | 1.0E-09 | 41.5 | 10.6 | 98.1 | 96.1 |
| | 1.0E-08 | 73.3 | 41.1 | 99.3 | 98.7 |

3. In Vivo Studies

The following summarizes in vivo hollow fiber assays performed by the NCI Developmental Therapeutics Program of the anti-cellular efficacy of the inventive XCLY-401759 mixture on several neoplastic tumor cell lines.

This testing was performed by the Biological Testing Branch of the Developmental Therapeutics Program. In these assays, human tumor cells as indicated were cultivated in polyvinylidene fluoride (PVDF) hollow fibers, and a sample of each cell line implanted into each of two physiologic compartments (intraperitoneal and subcutaneous) in mice. Each test mouse received a total of six fibers (3 intraperitoneally and 3 subcutaneously) representing 3 distinct cancer cell lines.

Three mice were treated with potential antitumor compounds at each of 2 test doses by the intraperitoneal route using a QD×4 treatment schedule. Vehicle controls consisted of 6 mice receiving the compound diluent only. The fiber cultures were collected on the day following the last day of treatment.

In assessing anticancer effects, viable cell mass was determined for each of the cell lines using a formazan dye (MTT) conversion assay. From this, the % T/C was calculated using the average optical density of the compound treated samples divided by the average optical density of the vehicle controls. The net increase in cell mass was determined for each sample.

In general, each compound was tested against a minimum of 12 human cancer cell lines. This represents a total of 4 experiments as each experiment contains 3 cell lines. The data is reported as %T/C for each of the 2 compound doses against each of the cell lines with separate values calculated for the intraperitoneal and subcutaneous samples.

Results of this in vivo assay are summarized below in Tables 8–11.

TABLE 8

Capillary Hollow Fiber Assay for XCLY-401759
NCI

EXP NO: HF597-0HF    HOST: Athymic Nudes
SEX: F    SOURCE/LINE: 1    SOURCE: APA

| | | | | | | % T/C (Net Growth) | | | | | |
|---|---|---|---|---|---|---|---|---|---|---|---|
| | | | | | | MDA-MB-435 | | OVCAR-5 | | SF-295 | |
| Grp No. | TREATMENT Dose/Units | Rt | Schedule | No. of Mice | No. of Fibers | IP | SC | IP | SC | IP | SC |
| 3 | 150.00 mg/kg/dose | IP | QD × 4, Day 4 | 3 | 2 | 93 | >100 | 82 | >100 | 91 | >100 |
| 4 | 100.00 mg/kg/dose | IP | QD × 4, Day 4 | 3 | 3 | 55 | 84 | 60 | >100 | 24 | 94 |
| VEHICLES | | | | | | | | | | | |

Grp 3 → 1 (Dose - 150.00) : In Saline : Tween 80 (0.05%) (Unknown) Inj. Vol.: 0.1 ml/10 gm body wt
Grp 4 → 1 (Dose - 100.00) : In Saline : Tween 80 (0.05%) (Unknown) Inj. Vol.: 0.1 ml/10 gm body wt COMMENTS for HF597-0-HF
This experiment is within acceptable quality control parameteres and is considered valid.

TABLE 9

Capillary Hollow Fiber Assay for XCLY-401759
NCI

EXPT NO: HF596-0-HF  
SEX: F  
SOURCE/LINE: 1  
HOST: Athymic Nudes  
SOURCE: APA

| Grp No. | TREATMENT Dose/Units | Rt | Schedule | No. of Mice | No. of Fibers | LOX IMVI IP | LOX IMVI SC | COLO 205 IP | COLO 205 SC | OVCAR-3 IP | OVCAR-3 SC |
|---|---|---|---|---|---|---|---|---|---|---|---|
| 3 | 150.00 mg/kg/dose | IP | QD × 4, Day 4 | 3 | 2 | | | | | 36 | |
|   |                   |    |               | 3 | 3 | −53 | >100 | 74 | 93 | | 99 |
| 4 | 100.00 mg/kg/dose | IP | QD × 4, Day 4 | 3 | 3 | −56 | −193 | 97 | 95 | 62 | 84 |

VEHICLES

Grp 3 → 1 (Dose - 150.00) : in Saline : Tween 80 (0.05%) (Unknown) Inj. Vol.: 0.1 ml/10 gm body wt  
Grp 4 → 1 (Dose - 100.00) : in Saline : Tween 80 (0.05%) (Unknown) Inj. Vol.: 0.1 ml/10 gm body wt Comments for HF596-0-HF  
This experiment is within acceptable quality control parameters and is considered valid.

TABLE 10

Capillary Hollow Fiber Assay for XCLY-401759
NCI

EXPT NO: HF594-0-HF  
SEX: F  
SOURCE/LINE: 1  
HOST: Athymic Nudes  
SOURCE: APA

| Grp No. | TREATMENT Dose/Units | Rt | Schedule | No. of Mice | No. of Fibers | NCI-H23 IP | NCI-H23 SC | MDA-MB-231 IP | MDA-MB-231 SC | SW-620 IP | SW-620 SC |
|---|---|---|---|---|---|---|---|---|---|---|---|
| 3 | 150.00 mg/kg/dose | IP | QD × 4, Day 3 | 3 | 3 | 72 | 85 | 90 | 99 | 88 | 83 |
| 4 | 100.00 mg/kg/dose | IP | QD × 4, Day 3 | 3 | 3 | 61 | >100 | 21 | >100 | 92 | >100 |

VEHICLES

Grp 3 → 1 (Dose - 150.00) : in Saline : Tween 80 (0.05%) (Unknown) Inj. Vol.: 0.1 ml/10 gm body wt  
Grp 4 → 1 (Dose - 100.00) : in Saline : Tween 80 (0.05%) (Unknown) Inj. Vol.: 0.1 ml/10 gm body wt Comments for HF594-0-HF  
This experiment is within acceptable quality control parameters and is considered valid.

TABLE 11

Capillary Hollow Fiber Assay for XCLY-401759
NCI

EXPT NO: HF595-0-HF  
SEX: F  
SOURCE/LINE: 1  
HOST: Athymic Nudes  
SOURCE: APA

| Grp No. | TREATMENT Dose/Units | Rt | Schedule | No. of Mice | No. of Fibers | NCI-H522 IP | NCI-H522 SC | UACC-62 IP | UACC-62 SC | U251 IP | U251 SC |
|---|---|---|---|---|---|---|---|---|---|---|---|
| 3 | 150.00 mg/kg/dose | IP | QD × 4, Day 3 | 3 | 3 | 75 | >100 | 62 | 60 | 58 | 94 |
| 4 | 100.00 mg/kg/dose | IP | QD × 4, Day 3 | 3 | 3 | 59 | 98 | 64 | >100 | 4 | 87 |

VEHICLES

Grp 3 → 1 (Dose - 150.00) : in Saline : Tween 80 (0.05%) (Unknown) Inj. Vol.: 0.1 ml/10 gm body wt  
Grp 4 → 1 (Dose - 100.00) : in Saline : Tween 80 (0.05%) (Unknown) Inj. Vol.: 0.1 ml/10 gm body wt Comments for HF595-0-HF  
This experiment is within acceptable quality control parameters and is considered valid.

We claim:
1. A compound of the formula:

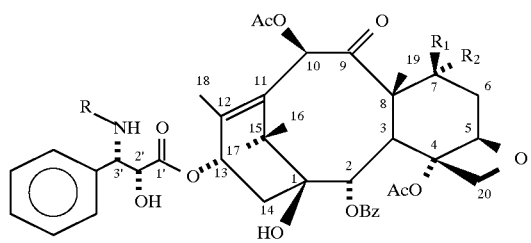

wherein R is selected from:

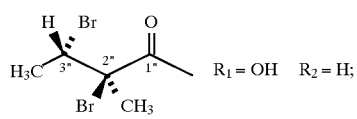 (I) $R_1 = OH$ $R_2 = H$;

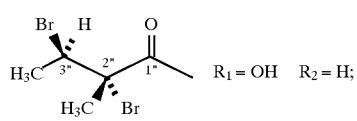 (II) $R_1 = OH$ $R_2 = H$;

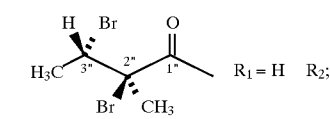 (III) $R_1 = H$ $R_2$;

and

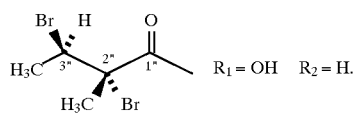 (IV) $R_1 = OH$ $R_2 = H$.

2. A pharmaceutical formulation which comprises as an active ingredient a compound of claim 1 or a pharmaceutically acceptable salt thereof, associated with one or more pharmaceutically acceptable carriers, excipients or diluents therefor.

3. A method for treating animal and human tumors which comprises administering to an animal or human in need thereof a tumor sensitive amount of a compound of claim 1.

4. The method of claim 3 wherein, in the compound administered,

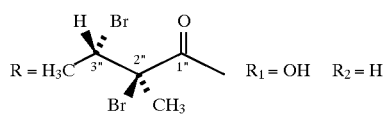 $R_1 = OH$ $R_2 = H$

5. The method of claim 3 wherein, in the compound administered,

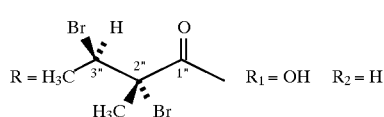 $R_1 = OH$ $R_2 = H$

6. The method of claim 3 wherein, in the compound administered,

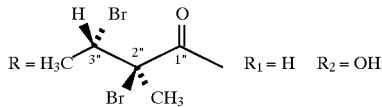 $R_1 = H$ $R_2 = OH$

7. The method of claim 3 wherein, in the compound administered,

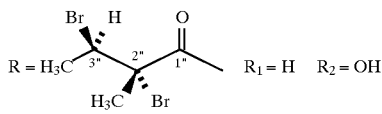 $R_1 = H$ $R_2 = OH$

8. A method for the production of a compound of the formula,

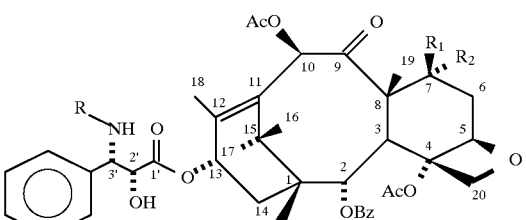

wherein R is selected from,

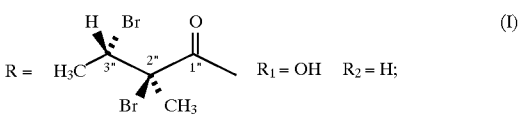 (I) $R_1 = OH$ $R_2 = H$;

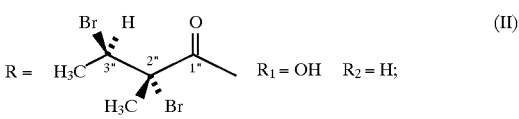 (II) $R_1 = OH$ $R_2 = H$;

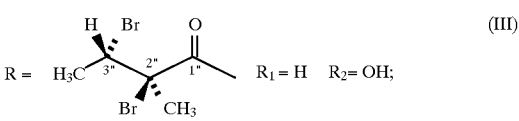 (III) $R_1 = H$ $R_2 = OH$;

and

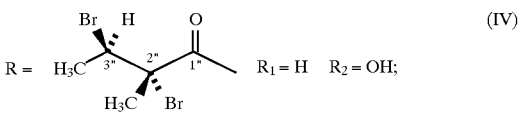 (IV) $R_1 = H$ $R_2 = OH$;

comprising brominating cephalomannine and/or 7-epi-cephalomannine under conditions effective to selectively brominate the 2", 3" unsaturated side-chain portion of cephalomannine and/or 7-epi-cephalomannine.

9. The method of claim 8, wherein a mixture of diastereomeric compounds I, II, III and IV is produced, and further comprising separating each of compounds I, II, III and IV from the mixture.

10. The method of claim 8 wherein the cephalomannine and/or 7-epi-cephalomannine is present in a mixture in any amount comprising paclitaxel and other taxane ring compounds.

11. The method of claim 10, wherein the bromination reaction is carried out in the dark at temperatures between about −20° C. to about 20° C.

12. The method of claim 10, wherein the reaction temperatures are between about −5° C. and about 5° C.

13. The method of claim 10, wherein the bromination reaction is carried out using a stoichiometric amount of bromine, relative to cephalomannine and/or 7-epi-cephalomannine concentration.

14. The method of claim 10, wherein the bromination reaction is carried out using a solution of bromine in a chlorinated solvent selected from the group consisting of $CCl_4$, $CHCl_3$, $ClCH_2CH_2Cl$ and $CH_2Cl_2$.

* * * * *